(12) United States Patent
Terada et al.

(10) Patent No.: US 7,052,875 B1
(45) Date of Patent: May 30, 2006

(54) STABLE GENE PREPARATIONS

(75) Inventors: Masaaki Terada, Tokyo (JP); Takahiro Ochiya, Tokyo (JP); Akihiko Sano, Osaka (JP); Akihiko Hisada, Chiba (JP); Shunji Nagahara, Osaka (JP)

(73) Assignees: Sumitomo Pharmaceutical Company, Limited, Osaka (JP); Koken Co., Ltd., Tokyo (JP)

( * ) Notice: Subject to any disclaimer, the term of this patent is extended or adjusted under 35 U.S.C. 154(b) by 0 days.

(21) Appl. No.: 09/701,013

(22) PCT Filed: May 19, 1999

(86) PCT No.: PCT/JP99/02595

§ 371 (c)(1),
(2), (4) Date: Jan. 12, 2001

(87) PCT Pub. No.: WO99/61063

PCT Pub. Date: Dec. 2, 1999

(30) Foreign Application Priority Data

May 22, 1998 (JP) .......................... 10-141426

(51) Int. Cl.
*C12P 19/34* (2006.01)
*A61K 38/17* (2006.01)
*C07H 21/02* (2006.01)
*C07C 59/255* (2006.01)
*C07C 59/265* (2006.01)

(52) U.S. Cl. ............... 435/91.1; 530/356; 536/23.1; 562/584; 562/585

(58) Field of Classification Search ............... 562/584, 562/585; 536/23.1, 1.11; 530/356; 435/91.1, 435/72, 100, 105, 109, 110; 424/78.8
See application file for complete search history.

(56) References Cited

U.S. PATENT DOCUMENTS 4,332,900 A * 6/1982 Manis et al. ............. 435/91.41
5,236,704 A * 8/1993 Fujioka et al. ............. 424/85.1
5,763,416 A * 6/1998 Bonadio et al. ............. 514/44

FOREIGN PATENT DOCUMENTS

| EP | 0 844 004 A1 | 5/1998 |
| JP | 4-370095 A | 12/1992 |
| JP | 5-331071 A | 12/1993 |
| JP | 5-345729 A | 12/1993 |
| JP | 9-71542 | 3/1997 |
| WO | WO 96/29096 * | 3/1996 |
| WO | WO 96/27393 A1 | 9/1996 |
| WO | WO9629096 * | 9/1996 |
| WO | WO 96/40265 * | 12/1996 |

OTHER PUBLICATIONS

Zatloukal, K. et al., Proc. Natl. Acad. Sci., vol. 91, pp/ 5148–5152, (1994).

M.S. Bruno et al., Abstract of Biotech 2001, Pharmaceutical Research, vol. 12 (1995), No. 9, Suppl., p. S79. (XP–001024486).

K. Fujioka et al., Journal of Controlled Release, vol. 33 (1995), No. 2, pp. 307–315.

K. Honma et al., Biochemical and Biophysical Research Communications, vol. 289 (2001), No. 5, pp. 1075–1081. (XP–002957375).

* cited by examiner

*Primary Examiner*—Shin-Lin Chen
(74) *Attorney, Agent, or Firm*—Birch, Stewart, Kolasch & Birch, LLP

(57) ABSTRACT

The invention is directed to the retention of the stability of formulations useful for a gene therapy during the preparation and preservation. In the invention, at least one saccharide and/or at least one non-hydrophobic amino acid and/or at least one organic acid having two or more carboxyl groups except amino acids, or a collagen or a gelatin and at least one amino acid are added to a gene formulation.

8 Claims, 19 Drawing Sheets

STABLE GENE PREPARATIONS

This application is the national phase under 35 U.S.C. § 371 of PCT International Application No. PCT/JP99/02595 which has a International filing date of May 19, 1999, which designated the United States of America.

FIELD OF THE INVENTION

The present invention relates to a stable gene formulation useful for a gene therapy. Particularly, the invention relates to a formulation which comprises a gene or a vector incorporated with a gene wherein the gene or the vector shows an improved stability during preparation and preservation.

BACKGROUND OF THE INVENTION

Gene therapy has been experimentally tried to clinically treat or prevent diseases, in particular genetic diseases. Gene therapy at the beginning has been studied using viruses as vectors, because the virus vectors were able to be introduced into cells with higher efficiency. After it was found that a plasmid DNA (pDNA) having an autonomously replicating ability could express gene information on the direct administration into muscle of animals, gene therapy using the plasmid DNAs has been investigated exclusively in light of the fact that pDNA possesses the higher safety, and may be more readily produced on a manufacturing scale than those of the virus vector.

Primary interests today in basic research for gene therapy using pDNAs are directed to an improvement in an introduction efficiency into cells, and an extension of a period of time during expression of gene information. For the purpose of the improvement in the introduction efficiency of pDNAs into cells, the method for encapsulating pDNA into a cationic liposome, and the method for preparing a complex with a polymer have been reported. For the purpose of the extension of the period during expression of gene information, the sustained-release formulation comprising collagen (Japanese Patent Publication (kokai) No. 71542/1997) or polyethylene vinyl acetate (Journal of Controlled release 47, 123 (1997)) as a carrier, each of which is highly biocompatible, has been reported. In practice, however, even if a gene formulation can serve these purposes, it would not make gene therapy widely prevalent unless the gene formulation can be produced commercially with a stability and an ability to maintain defined high qualities.

Biological activities of genes, active agents, in the gene formulations should be maintained securely during the preparation and the preservation of the formulations. It has been known that intra-muscular injection of closed circular pDNA which had been digested with a restriction enzyme results in an decreased gene information to the extent of about 10% of that provided by an inert closed circular pDNA. Consequently, in order to maintain the biological activities of genes it is important that a primary structure of pDNA should be retained all through the preparation and the preservation of the formulations, during which any unfavorable condition is expected.

Although some reports have discussed a stability of pDNA during the preservation in connection with the basic research of gene therapy as mentioned above [Proceedings of National Academy of Sciences of the USA, 93, 7305 (1996)], any systematical investigation about the preparation and the stability of gene formulations scarcely has been conducted yet. As shown in the test examples hereinafter, when the gene preparations comprising pDNA only, or comprising pDNA together with compounds useful for improving the introduction efficiency of pDNA or for extending the period of time during gene expression are exposed to lyophilization conditions usually employed in the formulation steps, or preservation conditions in which the qualities of the formulations would be securely maintained, an active agent (pDNA) is subject to degradation, and its biological activity is markedly impaired.

DISCLOSURE OF THE INVENTION

We had continued to perform the investigation aiming to provide a stable gene formulation, and found that addition of a saccharide and/or a non-hydrophobic amino acid and/or an organic acid having two or more carboxyl groups except amino acids to a solution of pDNA, or addition of an amino acid to a solution of pDNA which contains a collagen or a gelatin, drastically inhibit the pDNA degradation during the preservation of the solution, and/or through steps for lyophilizing the solution, and/or during the preservation of a lyophilized product from the solution. On the basis of the findings, we have accomplished the present inventions.

In one aspect, the present invention provides a stable gene formulation which comprises a desired gene or a vector incorporated with a desired gene as well as at least one saccharide and/or at least one non-hydrophobic amino acid and/or at least one organic acid having two or more carboxyl groups except amino acids.

The saccharide specifically includes a monosaccharide, a disaccharide, an oligosaccharide of a trisaccharide or higher, and a sugar alcohol thereof, and, more specifically, includes glucose, galactose, fructose, sucrose, maltose, lactose, trehalose, sorbitol, and mannitol.

The non-hydrophobic amino acid specifically includes glutamic acid, aspartic acid, and a salt thereof.

The organic acid having two or more carboxyl groups specifically includes an organic acid having two or three carboxyl groups, and a salt thereof, and more specifically includes citric acid and tartaric acid.

The vector incorporated with a desired gene includes a plasmid DNA.

The gene formulations according to the present invention may also contain a substance accelerating an introduction of the gene into a cell, or a pharmaceutically acceptable additive. The substance accelerating the introduction of the gene into a cell includes a cationic lipid, a cationic polymer, and a hydrophobic polymer. The pharmaceutically acceptable additive includes a biocompatible material.

The desired gene or the vector incorporated with the desired gene in the gene formulations of the invention may be borne on a biocompatible material. The biocompatible material includes a collagen, a gelatin, and a mixture thereof.

The present invention includes a gene formulation obtainable by drying, preferably lyophilizing, a preparation in a solution, a gel, or a suspension form which comprises a desired gene or a vector incorporated with a desired gene.

Further, the invention includes a gene formulation, which form is a solution, a gel, or a suspension, or a gene formulation which is prepared through a preparation in a solution, gel, or suspension form, wherein the amount of a saccharide, a non-hydrophobic amino acid, and an organic acid having two or more carboxyl groups except amino acids to the total amount of the solution, the gel or the suspension is about 1 w/v % or more.

In a further aspect, the present invention provides a process for stabilizing a gene formulation derived from a gene preparation comprising a desired gene or a vector incorporated with a desired gene, which comprises a step of adding at least one saccharide and/or at least one non-hydrophobic amino acid and/or at least one organic acid having two or more carboxyl groups except amino acids to the gene preparation.

In a still further aspect, the present invention provides a method for gene therapy, which comprises a step of administering the gene formulation of the present invention to a living body.

In a still further aspect, the present invention provides a stable gene formulation which comprises a desired gene or a vector incorporated with a desired gene, at least one amino acid, and a biocompatible material, particularly a collagen, or a gelatin. The gene formulation may also contain a substance accelerating the introduction of the gene into a cell, such as a cationic lipid, a cationic polymer, and a hydrophobic polymer. The present invention includes a gene formulation which comprises a desired gene or a vector incorporated with a desired gene borne on a biocompatible material, particularly a collagen, or a gelatin.

In this embodiment, the invention also includes a gene formulation obtainable by drying, particularly lyophilizing, a preparation in a solution, a gel, or a suspension form comprising a desired gene or a vector incorporated with a desired gene.

Further, the invention includes a gene formulation, which form is a solution, a gel, or a suspension, or a gene formulation which is prepared through a preparation in a solution, gel, or suspension form, wherein the amount of an amino acid to the total amount of the solution, the gel or the suspension is about 1 w/v % or more.

In a further aspect, the present invention provides a process for stabilizing a gene formulation derived from a gene preparation comprising a desired gene or a vector incorporated with a desired gene, and a biocompatible material, particularly a collagen, or a gelatin, which comprises a step of adding at least one amino acid to the gene preparation.

In a still further aspect, the present invention provides a method for gene therapy, which comprises a step of administering the gene formulation of the invention as described above to a living body.

DETAILED DESCRIPTION OF THE INVENTION

Figure 1:
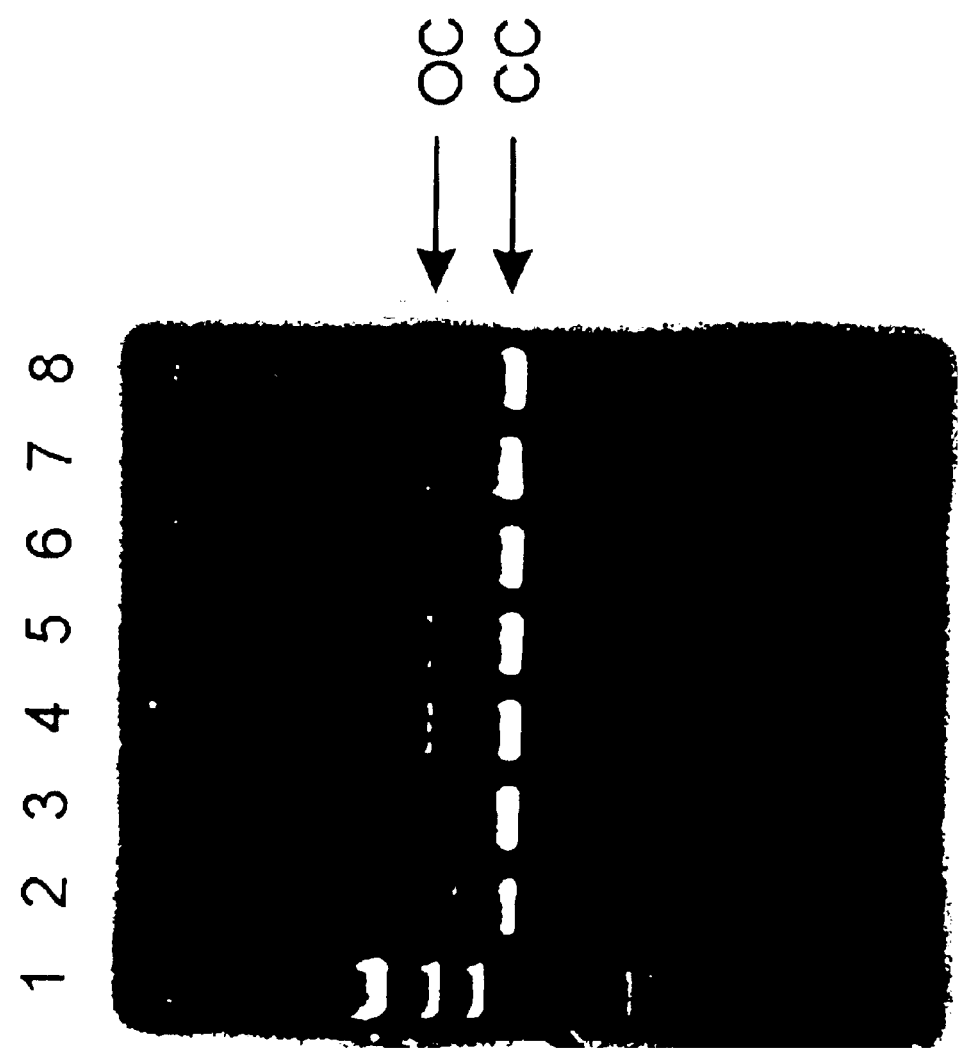
FIG. 1 is a photograph which shows the evaluation of the electrophoresed pCAHST-1 comprised in the gene formulations containing the amino acids, in the primary structure (Example 1).

As described above,: the present invention relates to a stable gene formulation which comprises a desired gene or a vector incorporated with a desired gene as well as at least one saccharide and/or at least one non-hydrophobic amino acid and/or at least one organic acid having two or more carboxyl groups; and to a stable gene formulation which comprises a desired gene or a vector incorporated with a gene, a collagen or a gelatin, and at least one amino acid. In another aspect, the present invention relates to a formulation which comprises the saccharide, the non-hydrophobic amino acid, and/or the organic acid, or which comprises the collagen or the gelatin, and the amino acid, together with the gene or the vector, wherein the gene or the vector demonstrates an increased stability, or an inhibited degradation.

The "desired gene" is any gene capable to be used in a gene therapy. The gene therapy means a therapy performed employing a gene. For example, the desired gene includes a gene encoding a gene information of a protein necessary to be expressed in the gene therapy, and an antisense sequence which inhibits the gene expression by base-pairing with a defined DNA or RNA within a cell. The antisense sequence may be employed without being incorporated into a vector.

The "vector incorporated with a desired gene" is preferably constructed to express an encoded gene information in a cell on introduction into the cell, and includes a vector comprising an element necessary to express the intended gene, such as a promoter, or an element capable to be integrated into a chromosome, which vector is exemplified by a pDNA.

The gene formulation may contain several kinds of vectors which are incorporated with different desired genes. Further, an individual vector may encode lots of gene information. The a mount of the vector contained in the gene formulation is not limited.

The gene encoding a protein necessary to be expressed in gene therapy includes any gene capable to be used in the treatment of a genetic disease, which is exemplified by, but is not limited to, a gene encoding an enzyme such as adenosine deaminase, thymidine kinase; a cytokine such as GM-CSF, IL-2; or fibroblast growth factor HST-1 (FGF4). The gene encoding other protein necessary to be expressed in the gene therapy includes, but is not limited to, a gene aimed at the treatment or the prevention for an infection or a tumor, which encodes a protein or a peptide serving as an antigen to induce immune response, i.e., the gene encoding the protein or the peptide capable of serving as an antigen such as mentioned above, for example, a gene encoding the surface protein an HA or an NA, or the nuclear protein NP of influenza virus, type C hepatitis virus E2 or NS 1 protein, type B hepatitis virus HBs antigen protein, type A hepatitis virus capsid protein VP1 or VP3, capsidoid protein, dengue virus Egp protein, RS virus F or G protein, G or N protein of the rabies virus structural protein, herpes virus gD protein, Japanese encephalitis virus E1 or pre-M protein, rotavirus coat protein VP7 or coat protein VP4, human immunodeficiency virus gp120 or gp160 protein, Leishmania major surface antigen protein, malaria circum sporozoite major surface antigen protein, Toxoplasma 54-kd or CS protein, cell surface protein PAc of caries-causing Streptococcus mutans; tumor regression antigens such as MAGE-1, MAGE-3, and BAGE, tissue-specific antigens such as tyrosinase, Mart-1, gp100 and gp75, p15, Mucl, CEA, HPV, E6, E7, HPR2/neu,etc.; and the gene of the nucleic acids which are described in "Immunization with DNA"; Journal of Immunological Methods, vol. 176, 1994, pages 145–152.

The "saccharide" includes a pharmaceutically acceptable monosaccharide, disaccharide, oligosaccharide of trisaccharide and higher, a sugar alcohol thereof, and a derivative thereof. The saccharide is not limited to any particular species as long as the addition to the gene formulation improves the stability of the formulation. The gene formulation of the invention may contain a mixture of two or more saccharides.

The saccharide is exemplified by a monosaccharide such as glucose, galactose, and fructose, and preferably glucose. The preferred disaccharide is exemplified by sucrose, maltose, lactose, and trehalose.

The sugar alcohol is exemplified by sorbitol, and mannitol, and preferably, mannitol.

The saccharide derivative includes a deoxy sugar, an amino sugar, a phosphate ester, and a disaccharide formed with thereof.

The non-hydrophobic amino acid means an amino acid having non-hydrophobic property among the amino acids. "Non-hydrophobic" means a property showing the higher compatibility with water, and is herein referred to as a property showing the higher compatibility with water than that of glycine. Indexing of the water-compatibility is described, for example, in Kyte, J.& Doolittele, R. F., 1982, J. Mol. Biol. 157, 105–132. According to the baseline described therein, hydrophobic amino acid includes glycine, alanine, methionine, phenylalanine, valine, leucine, and isoleucine. "Non-hydrophobic amino acid" includes preferably glutamine, asparagine, sodium glutamate, sodium aspartate, proline, and more preferably, glutamine, sodium glutamate, sodium aspartate.

The "amino acid" in the gene formulation of the present invention containing a collagen or a gelatin includes a pharmaceutically acceptable amino acid, a salt thereof, and a derivative thereof. The "amino acid" is not limited to the amino acids, as long as the addition to the formulation improves the stability of the formulation. The "amino acid" specifically includes not only an acidic amino acid such as glutamic acid and aspartic acid, but also lysine, arginine, and histidine, those which are classified as basic amino acids, and glycine, alanine, methionine, proline, cystine, serine, threonine, asparagine, glutamine, isoleucine, cysteine, tyrosine, tryptophan, and leucine, those which are other than acidic and basic amino acids. The "amino acid" in the present invention is irrespective of pH values in the solutions, and includes an amino acid having an additional basic or neutral side chain. The salt of the amino acid includes a sodium salt, a potassium salt, and the like. The preferred amino acid in the present formulation containing the collagen or the gelatin includes glutamine, asparagine, sodium glutamate, sodium aspartate, proline, arginine, histidine, lysine, and the like. The more preferred amino acid includes sodium glutamate, sodium aspartate, arginine, histidine, and lysine, those which decrease electrostatic interaction between a collagen and a DNA, and a still more preferred amino acid may be arginine, and histidine.

The "organic acid having two or more carboxyl groups" includes a pharmaceutically acceptable organic acid having two or more carboxyl groups (except an amino acid), a salt thereof, and a derivative thereof. The organic acid is not limited to any particular species as long as the addition to the formulation improves the stability of the formulation, provides that the organic acid excludes any amino acid.

The organic acid having two or more carboxyl groups, and salt thereof preferably includes an organic acid having two or three carboxyl groups, and salt thereof, and more preferably includes the organic acid which is a saturated or an unsaturated aliphatic acid. The organic acid having two or more carboxyl groups and salt thereof includes citric acid, tartaric acid, succinic acid, malic acid, fumaric acid, and a salt thereof, and preferably, citric acid, tartaric acid, and a salt thereof.

The gene formulation of the present invention includes a formulation comprising any one of the saccharide, the non-hydrophobic amino acid, and the organic acid having two or more carboxyl groups, as mentioned above, and a formulation comprising any combination of two of them, and all of them. In any case, the formulation of the invention may contain one or more saccharides, one or more amino acids, or one or more organic acids.

Total amount of the saccharide, the non-hydrophobic amino acid, and the organic acid having two or more carboxyl groups in the formulation containing each one of them, or a combination thereof, or amount of amino acid in the formulation containing the collagen or the gelatin is preferable an amount sufficient to inhibit the degradation of the gene or the vector comprised in the formulation of the present invention, but the amount can be optionally adjusted depending on the concentration or amount of the gene or vector, or practical form of the formulation. For example, the intended gene formulation may be obtained by lyophilizing a solution of pDNA at 10 μg/ml in 150 mM NaCl, 10 mM Tris-HCl (pH7.4), or, in case that the lyophilized formulation is preserved, it is preferable to add 1% (w/v) or more of a saccharide and/or a non-hydrophobic amino acid and/or an organic acid having two or more carboxyl groups to the solution. A range of pH of the formulation in a solution form before lyophilization or for practical use is pH5-pH8, preferably pH6-pH8, and more preferably pH7-pH8.

The gene formulation of the present invention may comprise a pharmaceutically acceptable additive or a substance capable to improve the gene expression. Consequently, the amounts of the saccharide, the amino acid and the organic acid also may depend on the amount and the kinds of the additives.

The pharmaceutically acceptable additive includes, but is not limited to, a biocompatible material, or an oil such as sesame oil, and squalene.

The desired gene or desired gene-carrying vector may be borne on the biocompatible material which is used as an additive, so as to provide a sustained-release formulation of the present invention. The biocompatible material as referred herein includes, but is not limited to, 1) a collagen, a gelatin, a fibrin, an albumin, a hyaluronic acid, a heparin, a chondroitin sulfate, a chitin, a chitosan, an alginic acid, a pectin, an agarose, a gum Arabic; 2) a polymer of glycolic acid, lactic acid or an amino acid, and a copolymer of two or more of these; and 3) a hydroxyapatite, a poly(methyl methacrylate), a polydimethylsiloxane, a polytetrafluoroethylene, a polypropylene, and a polyethylene. A collagen, a gelatin, or a mixture thereof is preferable.

The "be borne on" means that desired gene or desired gene-carrying vector is dispersed or taken in biocompatible material.

The "substance capable to improve gene expression" includes a substance accelerating introduction of the gene into a cell, or a substance accelerating introduction of the gene to nuclei. The former is exemplified by a cationic lipid, a cationic polymer, and a hydrophobic polymer. The cationic lipid includes DOTMA (N-[1-(2,3-dioleyloxy)propyl]-N-trimethyl ammonium chloride), DOSPA (2,3-dioleiloxy-N-[2-(spermine carboxamide)ethyl]-N,N-dimethyl-1-propane aminium trifluoroacetate), DDAB (dimethyldioctacrecyl ammonium bromide), TM-TPS (N, N', N", N'''-tetramethyl-N, N',N",N'''-tetrapalmityl spermine), DMRIE (1,2-dimyristyloxypropyl-3-dimethylhydroxyethyl ammonium bromide), and N-(α-trimethylammonioacetyl)-didodecy-D-glutamate chloride (Biochemical Biophysical Research Communication, 196, 1042 (1994)). Further, a cationic liposome comprising the cationic lipid as mentioned above and a neutral lipid such as DOPE (dioleoylphosphatidyl ethanolamine), and a mixture of the cationic lipid and cholesterol may be used. The "cationic polymer" is any polymer which electrostatically interacts with a gene, and includes a lipopolyamine such as DOGS (dioctadecylamidoglycyl spermine), a peptide such as AlkCWK$_{18}$, a cationic polyamino acid or a derivative thereof such as a polylysine and a derivative thereof (Proceedings of Academy Sciences of the USA, 89, 6094 (1992)), a polyethylenimine, and a polyamidamine dendrimer. The "hydrophobic polymer" is any polymer which hydrophobically interacts with a gene, and includes a polyvinyl alcohol, and a polyvinyl pyrrolidone. It also includes a peptide such as AlkCWK$_{18}$. The cationic liposome includes, but is not limited to, LIPOFECTAMINE (trademark, Life Technologies, Inc., Rockville, Md., USA) wherein 1:1 of DOSPA and DOPE is included, a liposome including 1:1 of DOTMA and DOPE, LIPOFECTACE (trademark, Life Technologies, Inc., Rockville, Md., USA) wherein 1:2.5 of DDAB and DOPE, and CELLFECTIN (trademark, Life Technologies, Inc., Rockville, Md., USA) wherein 1:1.5 of TM-TPS and DOPE. The mixture of cationic lipid and cholesterol as referred herein includes DMRIE-C (Life Technologies, Inc., Rockville, Md., USA) wherein DMRIE and cholesterol are mixed together at a molar ratio of 1:1. Alternatively, in order to suppress digestion of a gene in endosome within a cell, inactivated adenovirus capable to release the content of endosome, and CHEMS (cholesterol hemisuccinate morpholine salt) may be contained.

The substances accelerating introduction of gene into nuclei includes HMG-1,2 mixture (high mobility group-1,2 mixture: Experimental Medicine, 12, 184(1994)).

The form of the gene formulation of the present invention is not limited to any type of form, and may be a solution, a suspension, a gel, a sponge, a powder, a microparticle, a rod, a film.

As an example of a process for the preparation of the gene formulation in solution form, the following processes are exemplified;

1) a process for preparing a gene formulation in the form of homogenous solution, which comprises a step of adding a saccharide, and/or a non-hydrophobic amino acid, and/or an organic acid having two or more carboxyl groups to a solution of a desired gene or a vector carrying a desired gene, which optionally contains an additive, and a step of dissolving it (them) in the solution; or 2) a process for preparing a gene formulation in the form of homogenous solution, which comprises a step of adding a solution of a saccharide, and/or a non-hydrophobic amino acid, and/or an organic acid having two or more carboxyl groups to a solution of a desired gene or a vector carrying a desired gene, which optionally contains an additive, and a step of mixing the solutions.

Alternatively, the process for the preparation also includes a process for preparing a gene formulation in the form of homogenous solution, which comprises a step of adding a solution of a desired gene or a vector carrying a desired gene, which optionally contains an additive, and an amino acid or a solution of an amino acid, to a solution of a collagen or a gelatin, and a step of dissolving it in the solution or mixing the solutions.

As an example of a process for the preparation of the gene formulation in the form of microparticle, the following processes are exemplified;

1) a process for preparing a gene formulation, which comprises a step of spray-drying a solution of a desired gene or a vector carrying a desired gene, a saccharide, and/or a non-hydrophobic amino acid, and/or an organic acid having two or more carboxyl groups, and optionally an additive; or
2) a process for preparing a gene formulation, which comprises a step of lyophilizing a solution of a desired gene or a vector carrying a desired gene, a saccharide, and/or a non-hydrophobic amino acid, and/or an organic acid having two or more carboxyl groups, and optionally an additive, and a step of pulverizing the resultant sponge.

Alternatively, the process for the preparation also includes a process for preparing a gene formulation, which comprises a step of adding a solution of a desired gene or a vector carrying a desired gene, which optionally contains an additive, and an amino acid or a solution of an amino acid to a solution of collagen or gelatin, and a step of dissolving it in the solution or a step of mixing the solutions, followed by a step of spray-drying the resultant solution, or a step of lyophilizing the resultant solution and a step of pulverizing the lyophilized product.

As an example of a process for the preparation of the gene formulation in a rod form, the following processes are exemplified;
1) a process for preparing a gene formulation, which comprises a step of spray-drying a solution of a desired gene or a vector carrying a desired gene, a saccharide, and/or a non-hydrophobic amino acid, and/or an organic acid having two or more carboxyl groups, and optionally an additive, and a step of compressing and molding the resultant microparticles into a rod form;
2) a process for preparing a gene formulation, which comprises a step of lyophilizing a solution of a desired gene or a vector carrying a desired gene, a saccharide, and/or a non-hydrophobic amino acid, and/or an organic acid having two or more carboxyl groups, and optionally an additive, a step of pulverizing the resultant sponge, and a step of compressing and a step of molding the microparticles into a rod form;
3) a process for preparing a gene formulation, which comprises a step of lyophilizing a solution of a desired gene or a vector carrying a desired gene, a saccharide, and/or a non-hydrophobic amino acid, and/or an organic acid having two or more carboxyl groups, and optionally an additive, and a step of compressing and molding the resultant sponge into a rod form;
4) a process for preparing a gene formulation, which comprises a step of lyophilizing a solution of a desired gene or a vector carrying a desired gene, a saccharide, and/or a non-hydrophobic amino acid, and/or an organic acid having two or more carboxyl groups, and optionally an additive, a step of adding water or the like to the resultant sponge, and a step of kneading the mixture, followed by a step of extruding the kneaded mixture through a nozzle to form a bar, and a step of drying the same; and
5) a process for preparing a gene formulation, which comprises a step of spray-drying a solution of a desired gene or a vector carrying a desired gene, a saccharide, and/or a non-hydrophobic amino acid, and/or an organic acid having two or more carboxyl groups, and optionally an additive, a step of combining the microparticles with a silicone in a liquid form or a gum form which is soft suitably for blending, and adding a curing agent to the combination, followed by a step of extruding the combination through a nozzle to form a bar.

Alternatively, in case of the formulation containing a collagen or a gelatin, the preparations also include a similar preparation to those as described above except the usage of a collagen or a gelatin.

The gene formulations of the present invention may be administered via various procedures depending on a disease to be treated, a target organ, and the like. For example, the formulation can be administered subcutaneously, or intramuscularly, and can be administered directly to a target site such as kinder, liver, lung, brain, etc. where a disease exists. Organ-specific treatment may be accomplished by the direct administration to the disease site.

Effects provided by the gene formulation of the present invention containing a plasmid DNA (pDNA), which is an example of the formulation containing a vector carrying a desired gene are provided below;
1) When lyophilization, the typical procedure to prepare formulations, was performed on a solution containing merely pDNA, or a solution containing pDNA as well as an additive (a pharmaceutically acceptable additive, a biocompatible materials, a substance accelerating gene-introduction, and the like) other than a saccharide, a non-hydrophobic amino acid, and an organic acid having two or more carboxyl groups, degradation of pDNA was observed after the lyophilization in each case. On the other hand, when lyophilizing a solution comprising a saccharide and/or a non-hydrophobic amino acid and/or an organic acid having two or more carboxyl groups, degradation of pDNA therein was inhibited compared to the solution not comprising them;
2) When a solution containing merely pDNA, or a solution containing PDNA as well as an additive (a pharmaceutically acceptable additive, a biocompatible material, a substance accelerating gene-introduction, and the like) other than a saccharide, a non-hydrophobic amino acid, and an organic acid having two or more carboxyl groups was lyophilized, and the lyophilized product was preserved at 40° C., degradation of pDNA was observed after the lyophilization in each case. On the other hand, when preserving a lyophilizing product derived from a solution comprising a saccharide and/or a non-hydrophobic amino acid and/or an organic acid having two or more carboxyl groups, degradation of pDNA therein was inhibited compared to the solution not comprising them;
3) When lyophilization, the typical procedure to prepare formulations, was performed on a solution containing pDNA as well as a collagen or a gelatin, degradation of pDNA was observed after the lyophilization in each case. On the other hand, when lyophilizing a solution comprising an amino acid, degradation of pDNA therein was inhibited compared to the solution not comprising the same; and
4) When a solution containing pDNA as well as a collagen or a gelatin was lyophilized, and the lyophilized product was preserved at 40° C., degradation of pDNA was observed after the lyophilization in each case. On the other hand, when preserving a lyophilizing product derived from a solution comprising an amino acid, degradation of pDNA therein was inhibited compared to the solution not comprising them.

Effects of the composition including a saccharide and/or a non-hydrophobic amino acid and/or an organic acid having two or more carboxyl groups to stabilize the formulation can be observed not only in the drying step and at the time of preservation of the dried products, but also when the formulations are in solution forms. The effects are notable when the formulation comprises a cationic lipid, which are useful to improve introduction a ratio of a gene. This means;
5) When a solution containing merely pDNA, or a solution containing pDNA as well as a cationic lipid, and an additive (pharmaceutically an acceptable additive, a biocompatible material, a substance accelerating gene-introduction, and the like) other than a saccharide, a non-hydrophobic amino acid, and an organic acid having two or more carboxyl groups was preserved as it was, degradation of pDNA was observed in each case. On the other hand, when preserving a solution comprising a saccharide and/or a non-hydrophobic amino acid and/or an organic acid having two or more carboxyl groups, degradation of pDNA therein was inhibited compared to the solution not comprising them.

The effects of the present formulation to inhibit degradation of a gene or stabilizing the gene is specifically described in the test examples and Table 9 hereinafter.

The gene formulation in the form of rod, which comprises a pDNA encoding HST-1/FGF4, a collagen, and glucose as obtained according to the invention is intramuscularly injected to mouse, the pDNA was detected in blood for a period of 38 days after the injection, and the expression of HST-1 gene was observed in blood and at the injection site for a period of 60 days or more after the injection. On the other hand, when injecting the pDNA in solution form, the expression of HST-1 gene was observed for merely 30 days. The result shows not only that pDNA was released in a sustained-manner from the gene formulation in a rod form, comprising the collagen and glucose, and but also that the pDNA was retained in the gene formulation during a long period.

EXAMPLES

For further descriptions of the present invention, the following examples and test examples are presented, but these examples and test examples should not be construed to limit the scope of the invention.

The following examples describe the preparation of the formulation containing plasmid vector pCAHST-1 incorporated with the gene of fibroblast growth factor HST-1(FGF4) (Proc. Nati. Acad. Sci. USA, 84, 2980–2984(1987)). HST-1 gene product exhibits an action to megakaryocyte as blood platelet proliferating factor, and has been shown to effectively inhibit thrombocytopenia, the severe side effect of chemotherapy and radiotherapy for cancers (J. Clin. Invest., 96: 1125–2230, 1995, Oncogene, 13:9–19, 1996). pCAHST-1 is a plasmid vector wherein HST-1 gene is incorporated between the CAG promoter portion and the poly A sequence of the expression vector pCAGGS (Gene, 108, 193–200 (1991)). CAG promoter is described as a high expression vector in the Japanese Patent Publication (kokai) No. 168087/1991.

Example 1

Gene Formulations Containing Amino Acids (Dried State)

A solution of 10 μg/ml pCAHST-1 and 10 mg/ml glycine, alanine, monosodium glutamate, or lysine hydrochloride in 150 mM NaCl, 10 mM Tris-HCl (pH7.4) was prepared respectively. One ml portion of each solution was frozen at −40° C., and the frozen products were dried in vacuo overnight at room temperature. Like this, gene formulations in a dried state were obtained by lyophilization.

Example 2

Gene Formulations Containing Saccharides (Dried State)

A solution of 10 μg/ml pCAHST-1 and 10 mg/ml glucose, sucrose, maltose, lactose, or mannitol in 150 mM NaCl, 10 mM Tris-HCl (pH7.4) was prepared respectively. One ml portion of each solution was frozen at −40° C., and the frozen products were dried in vacuo overnight at room temperature. Like this, gene formulations in a dried state were obtained by lyophilization.

Example 3

Gene Formulations Containing Organic Acids Having Two or More Carboxyl Groups, and Amino Acids (Dried State)

A solution of 10 μg/ml pCAHST-1 and 10 mg/ml monosodium glutamate, sodium aspartate, sodium tartrate dihydrate, or tri-sodium citrate dihydrate in 150 mM NaCl, 10 mM Tris-HCl (pH7.4) was prepared respectively. One ml portion of each solution was frozen at −40° C., and the frozen products were dried in vacuo overnight at room temperature. Like this, gene formulations in a dried state were obtained by lyophilization.

Example 4

Gene Formulation Containing Saccharide and Cationic Lipid (Dried State)

A solution of 3 μg/ml pCAHST-1,24 μg/ml of DMRIE-C (Gibco BRL, substance for accelerating gene-introduction) and 10 mg/ml sucrose in 150 mM NaCl, 10 mM Tris-HCl (pH7.4 1 was prepared. One ml portion of the solution was frozen at −40° C., and the frozen product was dried in vacuo overnight at room temperature. Like this, a gene formulation in a dried state was obtained by lyophilization.

Example 5

Gene Formulations Containing Saccharides and Substances For Accelerating Gene-Introduction (Solution Form)

pCAHST-1, DMRIE-C (Gibco BRL), and glucose were combined with a solution of 150 mM NaCl, 10 mM Tris-HCl (pH7.4) until final concentrations reached 3 μg/ml, 24 μg/ml, and 10 mg/ml, respectively. Like this, a gene formulation in a solution form was obtained.

Example 6

Sustained-Release Gene Formulations (Gel Form)

To a solution (500 mg) of 0.1 w/w % atelocollagen, a solution of 100 μg/ml of pCAHST-1 (200 μl), and a solution of 10 mg/ml glucose (500 μl), sucrose, or monosodium glutamate were added and mixed. Then, the temperature of the each mixture was maintained at 37° C. to provide gene formulations in gel forms. Atelocollagen used in this example and the following examples and reference examples is available from KOKEN CO., LTD.

Example 7

Sustained-Release Gene Formulation (Sponge Form)

The gene formulation in a gel form containing glucose as prepared in Example 6 was lyophilized. This provided a gene formulation in a sponge form, which contains 500 μg of atelocollagen, 20 μl of pCAHST-1, 5 mg of glucose, sucrose, or sodium glutamate.

Example 8

Sustained-Release Gene Formulation (Rod Form)

To a solution (29.1 g) of 0.1 w/w % atelocollagen, water (60 g), and a solution of 11 mg/ml glucose (10 ml) were added and mixed. Then, a solution of 100 μg/ml of pCAHST-1 (80 ml) was added to the mixture, and mixed. After the solution thus obtained was lyophilized, an appropriate amount of a distilled water was added to the lyophilized product, and the mixture was kneaded. Then, the kneaded material was filled in a syringe, extruded, and dried to provide a formulation containing pCAHST-1 at 74% yield. This provided a gene formulation in a rod form, in which one mg of the formulation contains 17 μg of pCAHST-1, and 300 μg of glucose.

Reference 1

According to the procedure described in Example 1 except that the amino acid was not added, a composition in a dried state was prepared.

Reference 2

According to the procedure described in Example 4 except that sucrose was not added, a composition in a dried state was prepared.

Reference 3

According to the procedure described in Example 5 except that glucose was not added, a composition in a liquid form was prepared.

Reference 4

According to the procedures described in Examples 6 and 7 except that neither the solution of the saccharide nor the solution of monosodium glutamate was added, a composition in a sponge form was prepared, which contain 500 μg of atelocollagen, and 20 μg of pCAHST-1.

Reference 5

According to the procedure described in Example 8 except that the solution of glucose was not added, a dried composition in a bar form was prepared, in which one mg of the composition contain 20 μg of pCAHST-1.

Reference 6

According to the procedure described in Example 8 except that the solution of pCAHST-1 was not added, a dried composition in a bar form was prepared, in which one mg of the composition contain 300 μg of glucose.

Test Example 1

Effect of Amino Acids to Inhibit the Degradation of Gene at the Time of Lyophilization The gene formulations as prepared in Example 1, and the compositions as prepared in Reference 1 were dissolved respectively in water immediately after lyophilization, and the solutions were subjected to agarose gel electrophoresis to estimate the primary-structure of pCAHST-1s therein.

The agarose gel electrophoresis was performed using a horizontal electrophoresis unit (Mupid, ADVANCED Co.) on 0.8% agarose gel in TAE buffer. After the electrophoresis, the gel was stained in ethidium bromide, and photographed on a transilluminator. The picture was scanned in with a photo-scanner, and the intensity of all bands containing a supercoiled pDNA (CC), which primary structure was retained, and containing a fragmented pDNA (OC) was computed with an analytic software, to give a ratio of the CC, which represents retention ratio of the primary structure (CC retention ratio). In this case, CC retention ratio of untreated pDNA is estimated at 100. The method was also used in the following test examples when agarose gel electrophoresis was performed.

The result is shown in Table 1 and FIG. 1. In FIG. 1, CC is the supercoiled pCAHST-1, which primary structure was retained, whereas OC is the fragmented pCAHST-1. The lanes are the followings:

Lane 1: molecular weight marker (λHind III)

Lane 2: none (Reference 1)

Lane 3: monosodium glutamate (Example 1)

Lane 4: glycine (Example 1)

Lane 5: alanine (Example 1)

Lane 6: phenylalanine

Lane 7: lysine hydrochloride (Example 1)

Lane 8: untreated

TABLE 1

CC retention ratios in pCAHST-1 solutions containing an amino acid which had been lyophilized (% of untreated)

| Formula | CC retention ratio (% of untreated) |
| --- | --- |
| none (Reference 1) | 72 |
| monosodium glutamate (Example 1) | 96 |
| glycine (Example 1) | 79 |
| alanine (Example 1) | 83 |
| phenylalanine | 73 |
| lysine hydrochloride (Example 1) | 84 |
| untreated | 100 |

The result demonstrates that the addition of monosodium glutamate to the formulation provided the inhibition of degradation of pCAHST-1, compared to the formulation containing no amino acid.

Test Example 2

Effect of Saccharides to Inhibit the Degradation of Gene at the Time of Lyophilization The gene formulations as prepared in Example 2, and the composition as prepared in Reference 1 were separately dissolved in water immediately after lyophilization, and, in accordance with the procedure described in Test example 1, the solutions were subjected to agarose gel electrophoresis to estimate the primary-structure of pCAHST-1 therein. The result is shown in Table 2 and FIG. 2. The result demonstrates that the addition of glucose, sucrose, maltose, lactose, and mannitol to the formulation provided the drastic inhibition of degradation of pCAHST-1, compared to the formulation containing no saccharide.

TABLE 2

CC retention ratios in pCAHST-1 solutions containing a saccharide which had been lyophilized (% of untreated)

| Formula | CC retention ratio (% of untreated) |
| --- | --- |
| none (Reference 1) | 78 |
| glucose (Example 2) | 95 |
| sucrose (Example 2) | 96 |
| maltose (Example 2) | 95 |
| lactose (Example 2) | 100 |
| mannitol (Example 2) | 95 |
| untreated | 100 |

Figure 2:
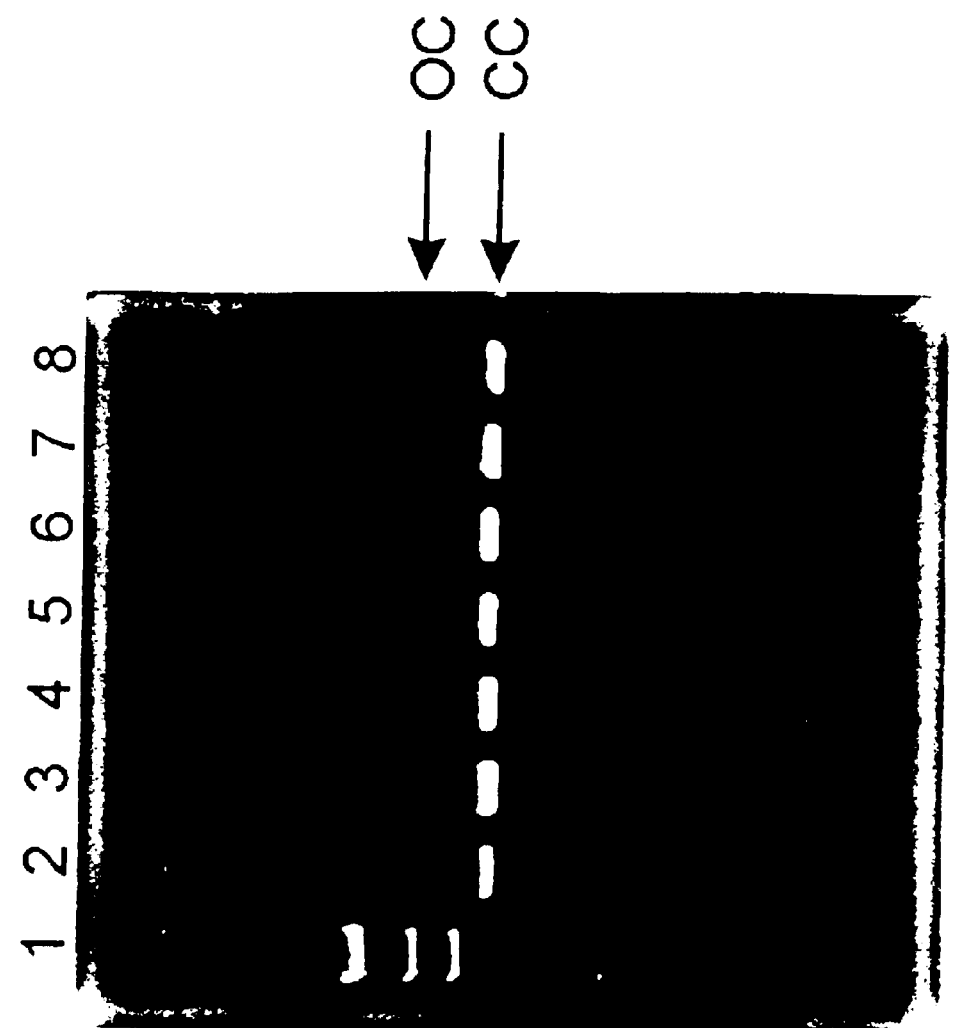
FIG. 2 is a photograph which shows the evaluation of the electrophoresed pCAHST-1 comprised in the gene formulations containing the saccharide, in the primary structure (Example 2).

In FIG. 2, CC is the supercoiled pCAHST-1, which primary structure was retained, whereas OC is the fragmented pCAHST-1. The lanes are the followings:

Lane 1: molecular weight marker (λHind III)

Lane 2: none (Reference 1)

Lane 3: glucose (Example 2)

Lane 4: sucrose (Example 2)

Lane 5: maltose (Example 2)

Lane 6: lactose (Example 2)
Lane 7: mannitol (Example 2)
Lane 8: untreated

Test Example 3

Effect of Organic Acids Having Two or More Carboxyl Groups and Amino Acids to Inhibit the Degradation of Gene at the Time of Lyophilization The gene formulations as prepared in Example 3, and the composition as prepared in Reference 1 were separately dissolyed in water immediately after lyophilization, and, in accordance with the procedure described in Test example 1, the solutions were subjected to agarose gel electrophoresis to estimate the primary-structure of pCAHST-1 therein. The result is shown in Table 3 and FIG. 3. The result demonstrates that the addition of monosodium glutamate, sodium aspartate, sodium tartrate dihydrate, or trisodium citrate dihydrate to the formulation provided the drastic inhibition of degradation of pCAHST-1, compared to the formulation containing no organic acid.

TABLE 3

CC retention ratios in pCAHST-1 solutions containing an organic acid having two or more carboxyl groups and an amino acid which had been lyophilized (% of untreated)

| Formula | CC retention ratio (% of untreated) |
|---|---|
| none (Reference 1) | 76 |
| monosodium glutamate (Example 3) | 103 |
| sodium aspartate (Example 3) | 91 |
| sodium tartrate dihydrate (Example 3) | 95 |
| trisodium citrate dihydrate (Example 3) | 102 |
| untreated | 100 |

Figure 3:
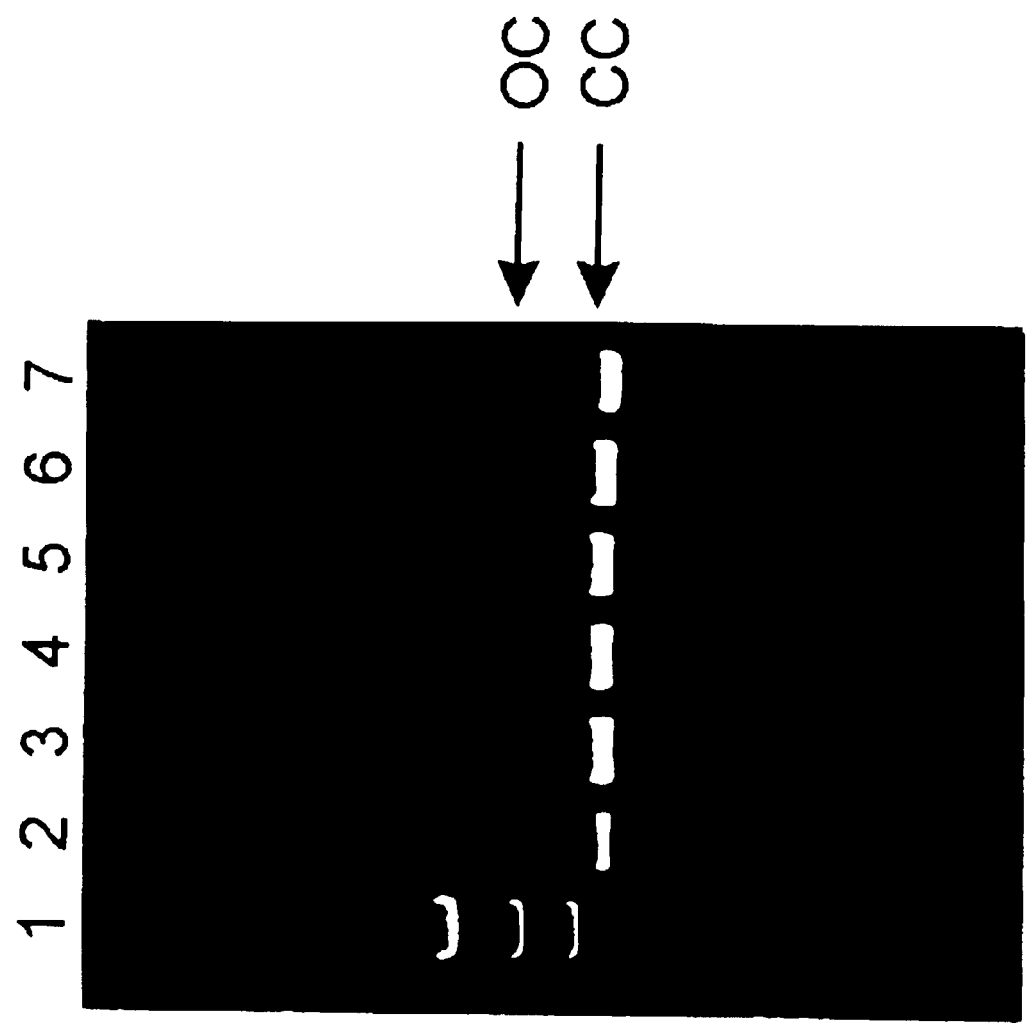
FIG. 3 is a photograph which shows the evaluation of the electrophoresed pCAHST-1 in the primary structure, which is comprised in the gene formulations containing the organic acid having two carboxyl groups, and the amino acid (Example 3).

In FIG. 3, CC is the supercoiled pCAHST-1, which primary structure was retained, whereas OC is the fragmented pCAHST-1. The lanes are the followings:

Lane 1: molecular weight marker (λHind III)
Lane 2: none (Reference 1)
Lane 3: monosodium glutamate (Example 3)
Lane 4: sodium aspartate (Example 3)
Lane 5: sodium tartrate dihydrate (Example 3)
Lane 6: trisodium citrate dihydrate (Example 3)
Lane 7: untreated Test Example 4

Effect of Sucrose to Inhibit the Degradation of Gene at the Time of Lyophilization of Gene Solution Containing Cationic Lipid The gene formulations as prepared in Example 4, and the composition as prepared in Reference 2 were separately dissolyed in water immediately after lyophilization, and, in accordance with the procedure described in Test example 1, the solutions were subjected to agarose gel electrophoresis to estimate the primary-structure of pCAHST-1 therein. The result is shown in Table 4 and FIG. 4. The result demonstrates that the addition of sucrose to the formulation provided the inhibition of degradation of pCAHST-1, compared to the formulation containing no sucrose.

TABLE 4

CC retention ratios in pCAHST-1 solutions containing a cationic lipid which had been lyophilized (% of untreated)

| Formula | CC retention ratio (% of untreated) |
|---|---|
| none (Reference 2) | 69 |
| sucrose (Example 2) | 100 |
| untreated | 100 |

Figure 4:
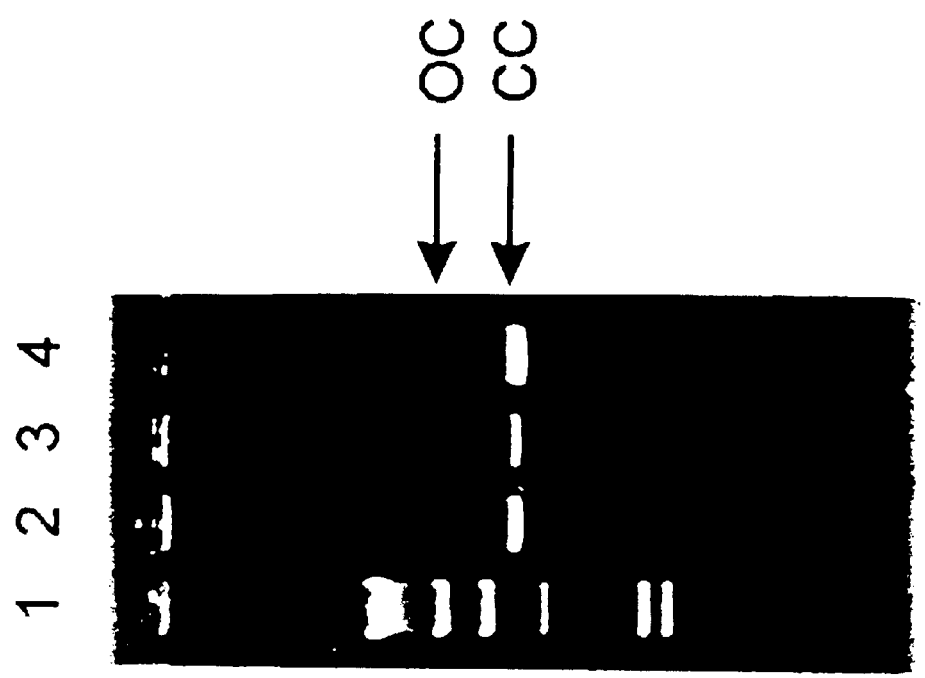
FIG. 4 is a photograph which shows the evaluation of the electrophoresed pCAHST-1 in the primary structure, which is comprised in the gene formulations containing the saccharide, and substance accelerating gene introduction (Example 4).

In FIG. 4, CC is the supercoiled pCAHST-1, which primary structure was retained, whereas OC is the fragmented pCAHST-1. The lanes are the followings:

Lane 1: molecular weight marker (λHind III)
Lane 2: none (Reference 2)
Lane 3: sucrose (Example 4)
Lane 4: untreated Test Example 5

Effect of Glucose to Inhibit the Degradation of Gene at the Time of Preservation at 40° C. (1)

The gene formulation containing glucose of the formulations as prepared in Example 2, and the composition as prepared in Reference 1 were preserved for one, two, and four weeks at 40° C. In accordance with the procedure described in Test example 1, the primary-structure of pCAHST-1 therein was estimated by agarose gel electrophoresis after the preservations. The result is shown in Table 5 and FIG. 5. The result demonstrates that the addition of glucose to the formulation drastically improved the preservative stability of pCAHST-1 under the specified conditions, compared to the formulation containing no glucose.

TABLE 5

CC retention ratios in dried products of pCAHST-1 containing glucose after preservation at 40° C. (% of untreated)

| Formula | CC retention ratio (% of untreated) |
|---|---|
| none (Reference 1/for one week at 40° C.) | 67 |
| none (Reference 1/for two weeks at 40° C.) | 56 |
| none (Reference 1/for four weeks at 40° C.) | 34 |
| glucose (Example 2/for one week at 40° C.) | 92 |
| glucose (Example 2/for two weeks at 40° C.) | 91 |
| glucose (Example 2/for four weeks at 40° C.) | 71 |
| untreated | 100 |

Figure 5:
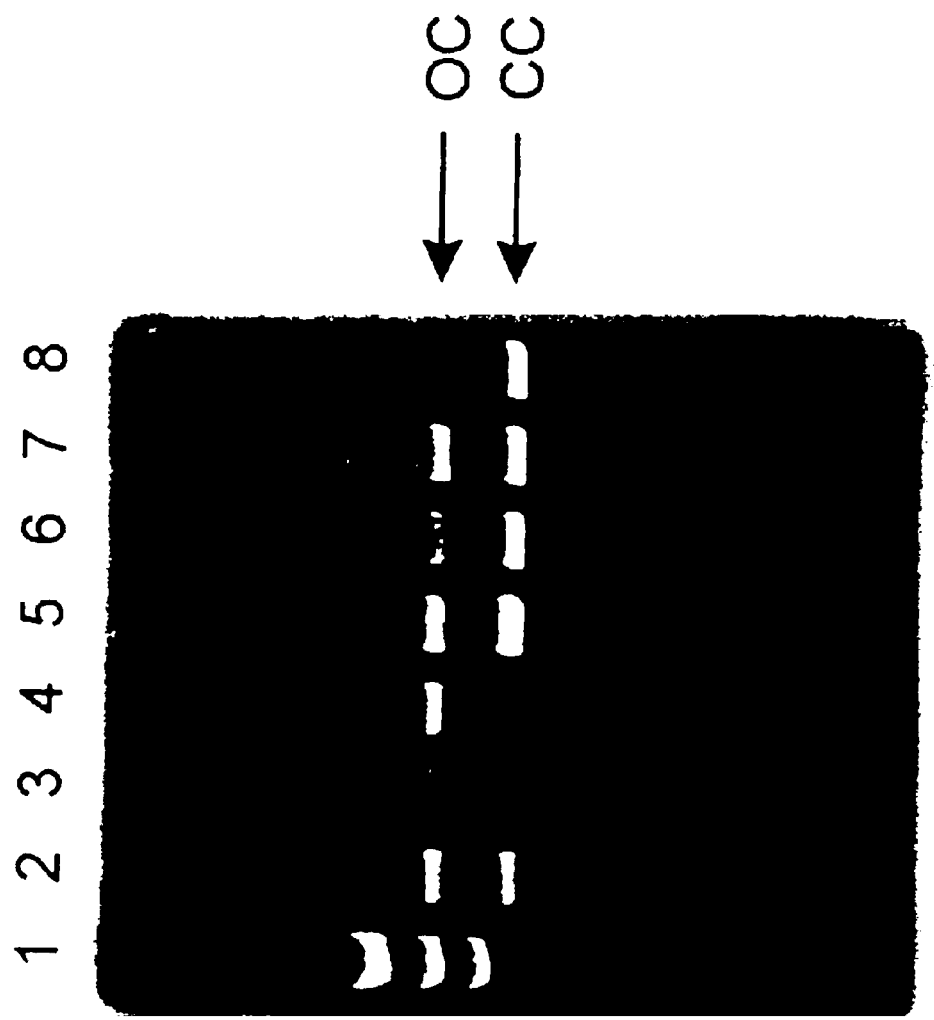
FIG. 5 is a photograph which shows the evaluation of the electrophoresed pCAHST-1 in the primary structure comprised in the gene formulations containing the saccharide (Example 2), which formulations have been preserved at 40° C.

In FIG. 5, CC is the supercoiled pCAHST-1, which primary structure was retained, whereas OC is the fragmented pCAHST-1. The lanes are the followings:

Lane 1: molecular weight marker (λHind III)
Lane 2: none (Reference 1/for one week at 40° C.)
Lane 3: none (Reference 1/for two weeks at 40° C.)
Lane 4: none (Reference 1/for four weeks at 40° C.)
Lane 5: glucose (Example 2/for one week at 40° C.)
Lane 6: glucose (Example 2/for two weeks at 40° C.)
Lane 7: glucose (Example 2/for four weeks at 40° C.)
Lane 8: untreated Test Example 6

Effect of Sucrose to Inhibit the Degradation of Gene at the Time of Preservation at 37° C.

The gene formulation as prepared in Example 4, and the composition as prepared in Reference 2 were preserved for four weeks at 37° C. The primary-structure of pCAHST-1 was estimated by agarose gel electrophoresis after the preservation as described in Test example 1. The result is shown in Table 6 and FIG. 6. The result demonstrates that the addition of sucrose to the formulation drastically improved the preservative stability of pCAHST-1 under the specified condition, compared to the formulation containing no sucrose.

TABLE 6

CC retention ratios in dried products of the solutions of pCAHST-1 containing cationic lipid after preservation for four weeks at 37° C. (% of untreated)

| Formula | CC retention ratio (% of untreated) |
| --- | --- |
| none (Reference 2/for four weeks at 37° C.) | 8.5 |
| sucrose (Example 4/for four weeks at 37° C.) | 67 |
| untreated | 100 |

Figure 6:
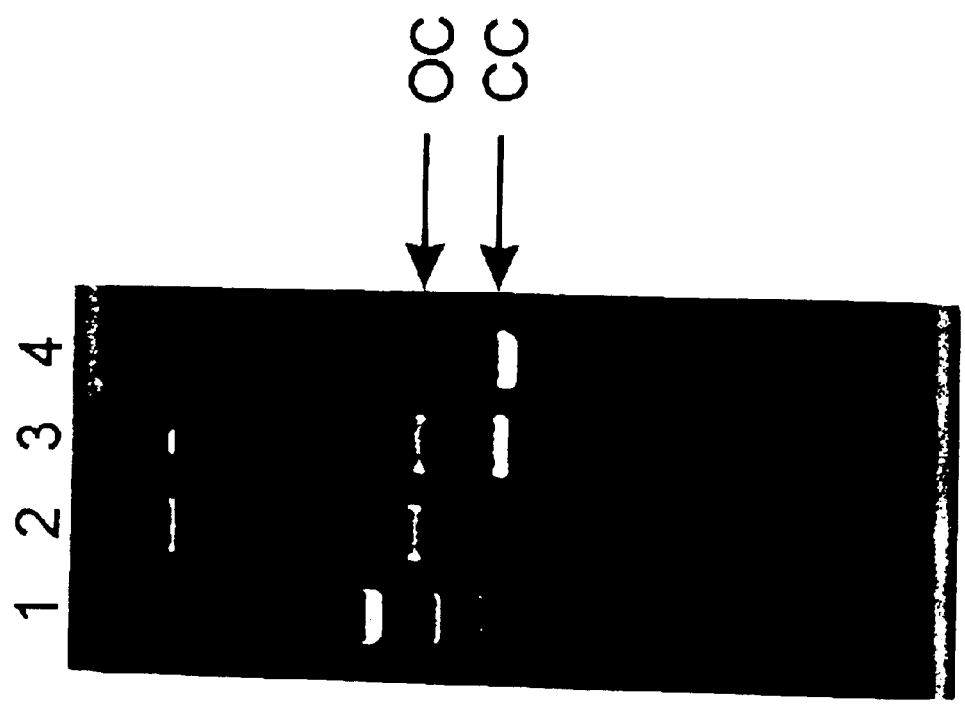
FIG. 6 is a photograph which shows the evaluation of the electrophoresed pCAHST-1 in the primary structure comprised in the gene formulations containing the saccharide and the substance accelerating gene introduction (Example 4), which formulations have been preserved for four weeks at 37° C.

In FIG. 6, CC is the supercoiled pCAHST-1, which primary structure was retained, whereas OC is the fragmented pCAHST-1. The lanes are the followings:

Lane 1: molecular weight marker (λHind III)
Lane 2: none (Reference 2/for four weeks at 37° C.)
Lane 3: sucrose (Example 4/for four weeks at 37° C.)
Lane 4: untreated Test Example 7

Effect of Glucose to Inhibit the Degradation of Gene at the Time of Preservation at 40° C. (2)

Figure 7:
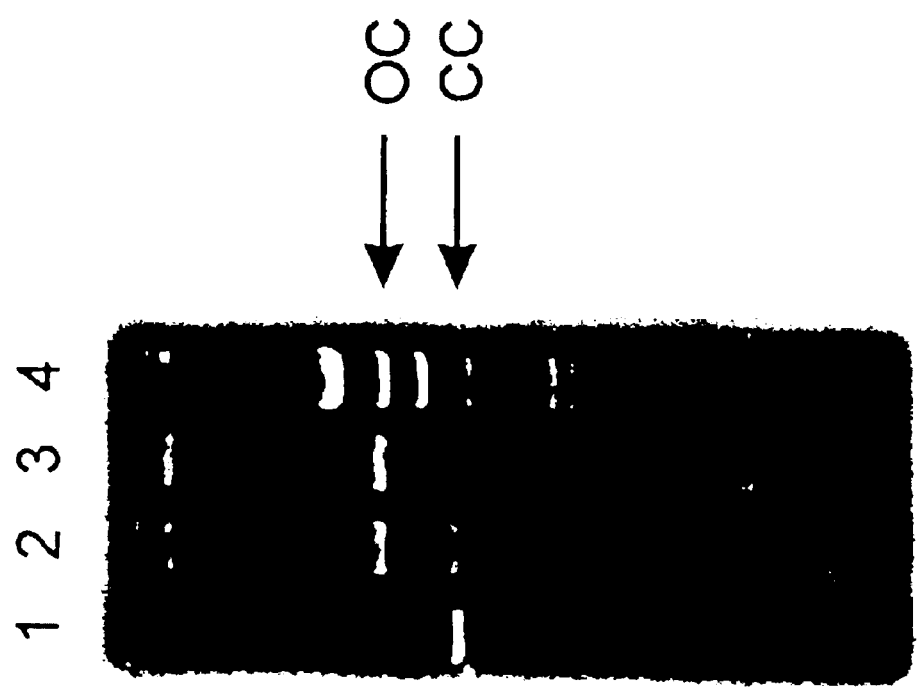
FIG. 7 is a photograph which shows the evaluation of the electrophoresed pCAHST-1 in the primary structure comprised in the gene formulations in a solution form containing the saccharide and the substance accelerating gene introduction (Example 5), which formulations have been preserved for four weeks at 40° C.

The gene formulation in liquid form as prepared in Example 5, and the composition as prepared in Reference 3 were preserved for four weeks at 40° C. The primary-structure of pCAHST-1 was estimated by agarose gel electrophoresis after the preservation as described in Test example 1. The result is shown in FIG. 7. The result demonstrates that the addition of glucose to the formulation drastically improved the preservative stability of pCAHST-1 under the specified condition, compared to the formulation containing no glucose, which result is similar to that of the dried formulation of Test example 5.

In FIG. 7, CC is the supercoiled pCAHST-1, which primary structure was retained, whereas OC is the fragmented pCAHST-1. The lanes are the followings:

Lane 1: untreated
Lane 2: glucose (Example 5/for four weeks at 40° C.)
Lane 3: none (Reference 3/for four weeks at 40° C.)
Lane 4: molecular weight marker (λHind III)

Test Example 8

Effect of Saccharides, etc. to Inhibit the Degradation of Gene in the Presence of Collagen (1)

Figure 8:
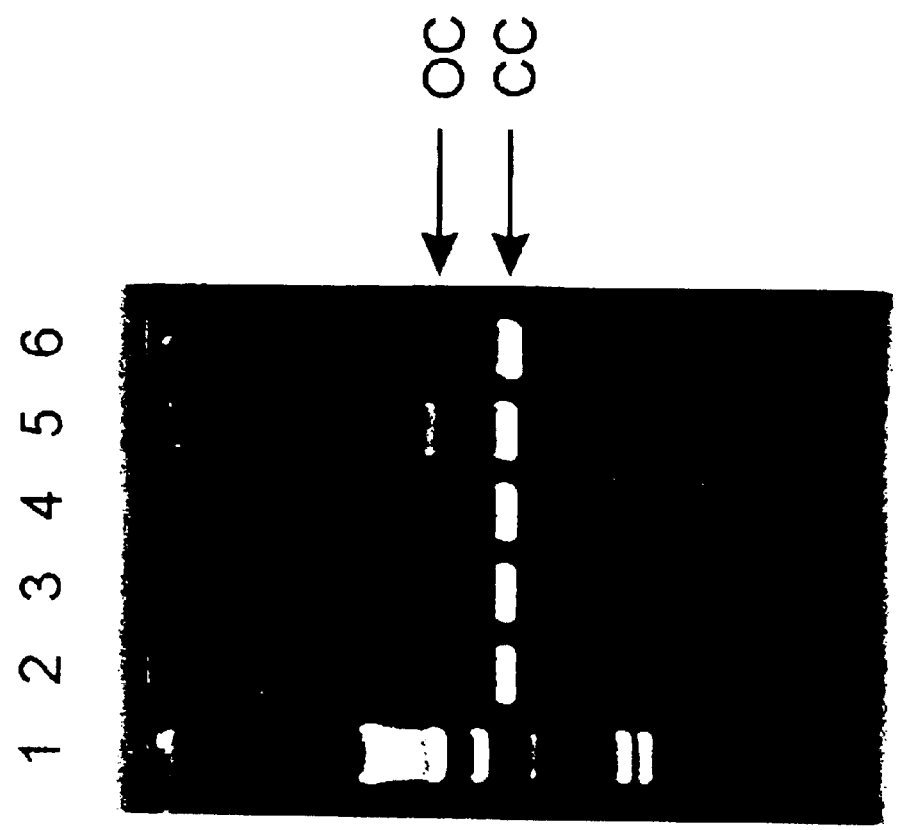
FIG. 8 is a photograph which shows the evaluation of the electrophoresed pCAHST-1 in the primary structure, which is comprised in the gene formulations in a sponge form containing collagen (Example 7).

The gene formulations in a sponge form as prepared in Example 7, and the composition in a sponge form as prepared in Reference 4 were separately dissolved in a solution of 150 mM NaCl, 10 mM Tris-HCl (pH7.4) under heating, and the solutions were treated with a collagenase. After the treatment, the solutions were subjected to agarose gel electrophoresis to estimate the primary-structure of pCAHST-1 therein, in accordance with the procedure described in Test example 1. As a result, the addition of glucose, sucrose, and monosodium glutamate to the formulation provided the drastic inhibition of degradation of pCAHST-1, compared to the formulation containing no saccharide (FIG. 8, Table 7).

TABLE 7

CC retention ratios in pCAHST-1 solutions containing a collagen, a saccharide, and an amino acid, which had been lyophilized (% of untreated)

| Formula | CC retention ratio (% of untreated) |
| --- | --- |
| none (Reference 4) | 85 |
| glucose (Example 7) | 94 |
| sucrose (Example 7) | 95 |
| monosodium glutamate (Example 7) | 95 |
| untreated | 100 |

In FIG. 8, CC is the supercoiled pCAHST-1, which primary structure was retained, whereas OC is the fragmented pCAHST-1. The lanes are the followings:

Lane 1: molecular weight marker (λHind III)
Lane 2: glucose (Example 7)
Lane 3: sucrose (Example 7)
Lane 4: monosodium glutamate (Example 7)
Lane 5: none (Reference 4)
Lane 6: untreated Test Example 9

Effect of Saccharide, etc. to Inhibit the Degradation of Gene in the Presence of Collagen (2)

Figure 9:
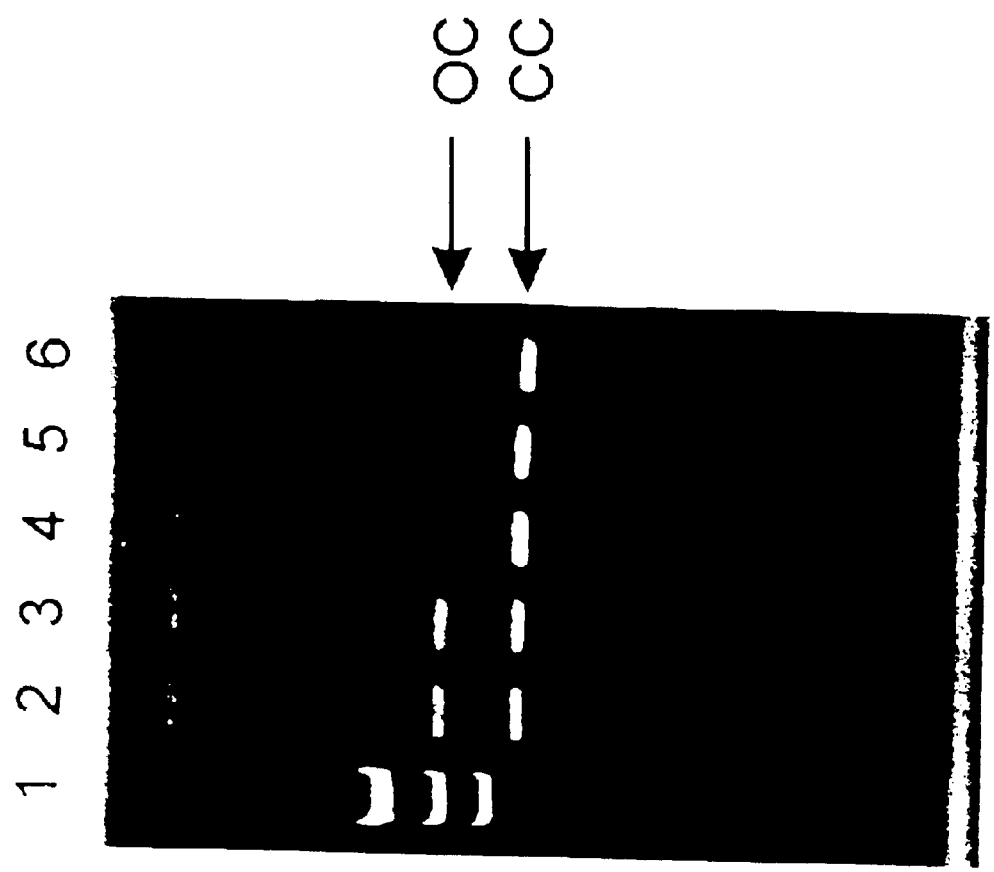
FIG. 9 is a photograph which shows the evaluation of the electrophoresed pCAHST-1 in the primary structure, which is comprised in the gene formulations in a rod form containing collagen (Example 8).

The gene formulations in a rod form as prepared in Example 8, and the composition in a rod form as prepared in Reference 5 were separately dissolved in a solution of 137 mM NaCl, 2.7 mM KCl, 25 mM Tris-HCl (pH7.4) under heating, and the solutions were treated with a collagenase. After the treatment, the solutions were subjected to agarose gel electrophoresis to estimate the primary-structure of pCAHST-1 therein, in accordance with the procedure described in Test example 1. As a result, the addition of glucose to the formulation provided the drastic inhibition of degradation of pCAHST-1, compared to the formulation containing no glucose (FIG. 9, Table 8).

TABLE 8

CC retention ratios of pCAHST-1s contained in the compositions in a rod form (% of untreated)

| Formula | CC retention ratio (% of untreated) |
| --- | --- |
| none (Reference 5) | 66 |
| glucose (Example 8) | 92 |
| untreated | 100 |

In FIG. 9, CC is the supercoiled pCAHST-1, which primary structure was retained, whereas OC is the fragmented PCAHST-1. The lanes are the followings:

Lane 1: molecular weight marker (λHind III)
Lane 2: none (1) (Reference 5)
Lane 3: none (Reference 5)
Lane 4: glucose (1) (Example 8)
Lane 5: glucose (2) (Example 8)
Lane 6: untreated Test Example 10

Gene Introduction of Stable Gene Formulation

The gene formulation in a rod form (atelocollagen/ glucose-pCAHST-1) as prepared in Example 8, and the composition in a rod form (atelocollagen-pCAHST-1) as prepared in Reference 5 were cut into the portions containing 50 μg of pCAHST-1. These were administered to the right femoral muscle of ICR mice (female, aged 6–7 weeks) (group 1, the gene formulation of Example 8; group 2, the composition of Reference 5) respectively. Further, 100 μl of a phosphate buffer containing 50 μg of pCAHST-1 was administered to the right femoral muscle of ICR mice (group 3).

In order to examine the in vivo sustained-release effect, three parameters, namely, detection of pCAHST-1 in blood, amount of HST-1 in blood and at the administration site, and counts of platelet in blood were utilized. pCAHST-1 in blood was detected by PCR, amount of HST-1 in blood and at the administration site (in muscle) were determined by ELISA, and platelets in blood were counted by micrography, each of them conducting with the time course.

PCR was conducted by Ampridirect method (Shimazu Corp.) utilizing a probe capable to detect the 262 bp sequence in pCAHST-1 (about 8 kbp). Limit of measurement was 1 pg/5 μl in Southern blotting, and 2 pg/5 μl in ethidium bromide staining. ELISA was conducted using FGF4 kit (R&D systems, U.S.A., limit of measurement: 20 pg/ml). Platelets in blood were counted by micrography after the blood taken was treated to decompose the blood cell components other than platelet.

Figure 10:
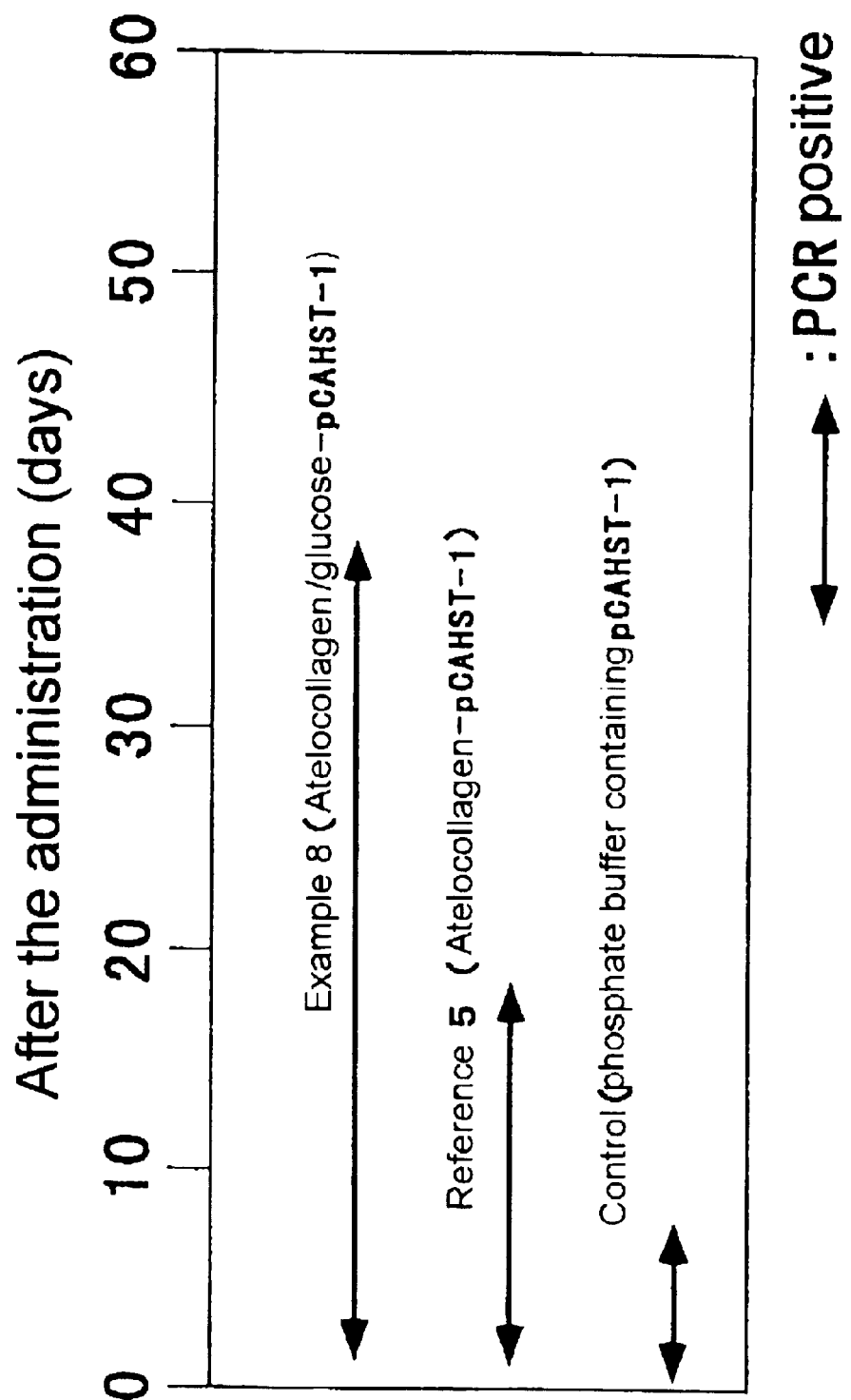
FIG. 10 is a graph which shows the periods of time during which the pCAHST-1 in the gene formulations in the rod form (Example 8) can be detected in blood.

The result of determination of pCAHST-1 in blood by PCR is shown in FIG. 10. In group 1, pCAHST-1 appeared in blood six hours after administration, and the detection lasted for 38 days after that. In group 2, pCAHST-1 appeared in blood six hours after administration, and the detection lasted for 18 days after that. In group 3, pCAHST-1 was detected merely for seven days after administration.

Figure 11:
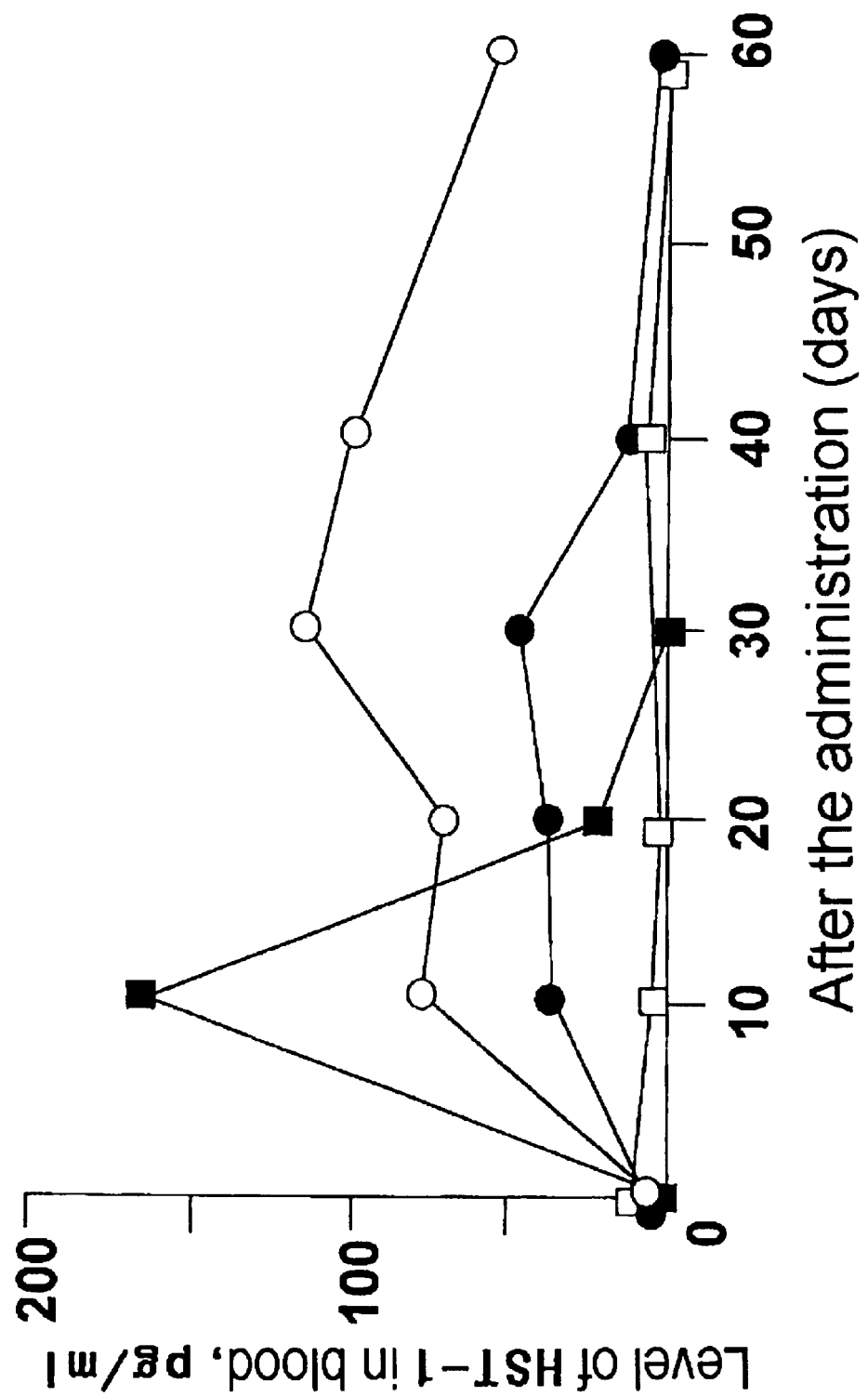
FIG. 11 is a graph which shows the change of concentrations of HST-1 released from the gene formulations in the rod form (Example 8) in blood with the time course.
Figure 12:
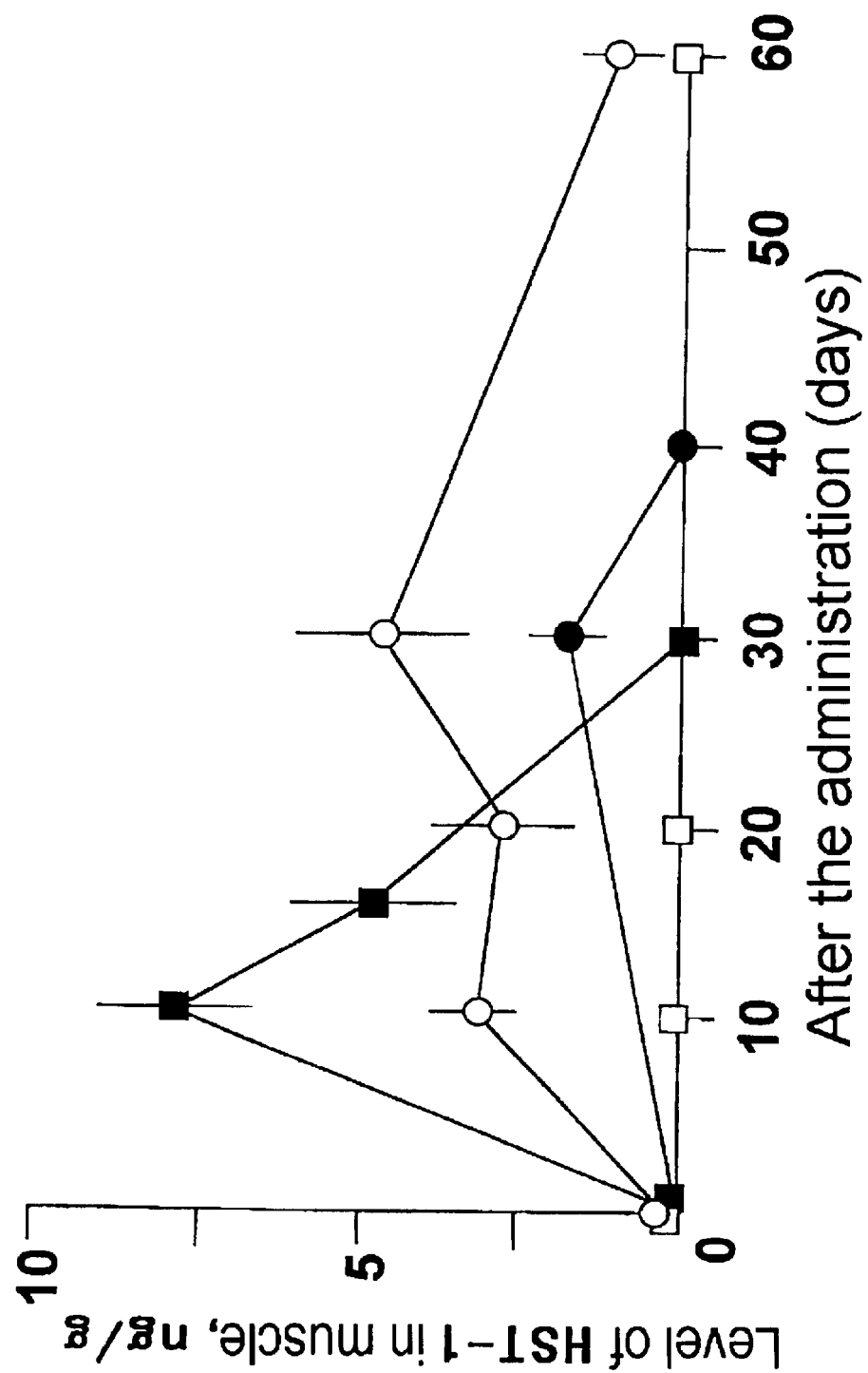
FIG. 12 is the results of Text example 10, and is a graph which shows the change of amount of HST-1 at the injection site with the time course.

The results of HST-1 amount in blood and at the administration site are shown in FIGS. 11 and 12. In FIG. 11, the symbols represent the followings: open circle, atelocollagen/glucose-pCAHST-1 (group 1, Example 8); solid circle, atelocollagen-pCAHST-1 (group 2, Reference 5); solid square, phosphate buffer containing pCAHST-1 (group 3, control); open square, atelocollagen/glucose (Reference 6).

In FIG. 12, the symbols represent the followings: open circle, atelocollagen/glucose-pCAHST-1 (group 1, Example 8); solid circle, atelocollagen-pCAHST-1 (group 2, Reference 5); solid square, phosphate buffer containing pCAHST-1 (group 3, control); open square, atelocollagen/glucose (Reference 6).

Group 1 shows that the amount of HST-1 both in blood and at the administration site increased after administration, reached a maximum on the 30th day after administration, and then gradually decreased, the detection lasting even after 60 days. Similarly to group 1, group 2 shows that the amount of HST-1 in blood and at the administration site increased after administration, reached a maximum on the 30th day after administration, and then gradually decreased to reach the limit of measurement after 40 days. The total amount of HST-1 produced was smaller than that of group 1. Group 3 shows that the amount of HST-1 in blood and at the administration site increased after administration, reached a maximum on the 10th day after administration, then gradually decreased, and no HST-1 was detected after 30 days.

As a result of determinations of platelet counts in blood with the time course (FIG. 13), group 1 shows that the platelet counts increased after administration, reached a maximum on the 30th day after administration, and then gradually decreased, tendency to the increase of platelet counts keeping even after 60 days. Group 2 shows that the platelet counts gradually increased after administration, reached a maximum on the 14th day after administration, then decreased, and tendency to the increase of platelet counts kept even after 28 days, which level is lower. Group 3 shows that the platelet counts increased after administration, reached a maximum on the 10th day after administration, then gradually decreased, and returned to the normal level on the 25th day.

Figure 13:
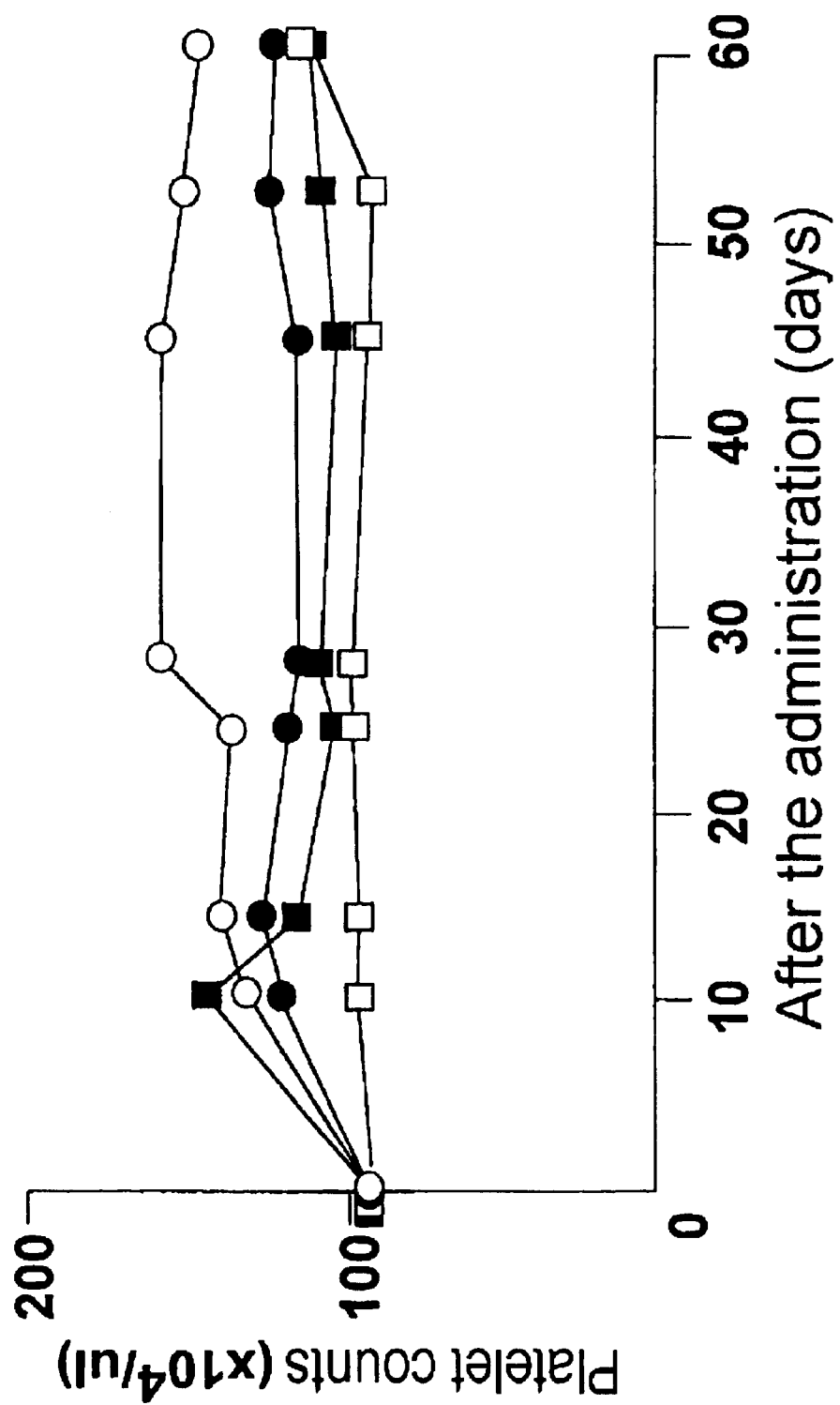
FIG. 13 is the results of Text example 10, and is a graph which shows the change of counts of blood platelet in blood with the time course.

In FIG. 13, the symbols represent the followings: open circle, atelocollagen/glucose-pCAHST-1 (group 1, Example 8); solid circle, atelocollagen-pCAHST-1 (group 2, Reference 5); solid square, phosphate buffer containing pCAHST-1 (group 3, control); open square, atelocollagen/glucose (Reference 6).

As a control, the composition containing no pCAHST-1 as prepared in Reference 6 was administered into the right femoral muscle of mice as described above, and then, amount of HST-1 in blood and at the administration site were determined by ELISA, and blood platelets were counted with the time course. As a result, HST-1 was detected neither in blood nor at the site during a period of determination. Further, no blood platelet count increased during a period of determination. This demonstrates that the production of HST-1 and the increase in blood platelet count as obtained in group 1 using the gene formulation of Example 8 and group 2 were caused by introduction of pCAHST-1 contained in the formulation into cells, and subsequent expression of the gene information of HST-1 within the cells.

From the results of groups 1 and 3, it is revealed that expression of HST-1 in the body, and biological activity of the produced HST-1 are temporary in case of the administration of pCAHST-1 alone, and, on the contrary, the gene formulation of Example 8 enables the sustained-releasing and the stable maintenance of pCAHST-1 in the body for a long period of time, thus making it possible to extend an expression period of HST-1, and to retain a biological activity of the produced HST-1 for a long period of time.

From the results obtained in groups 1 and 2, it is revealed that both gene formulations of Example 8 and Reference 5 enable the sustained-releasing of pCAHST-1 and the extension of an expression period of HST-1, compared to the administration of pCAHST-1 alone, and that the gene formulation containing glucose of Example 8 enables the stable maintenance of pCAHST-1 in the body, and the extension of an expression period of HST-1 at a high production level, thus making it possible to retain a biological activity of HST-1 at a high level for a long period of time, compared to the gene formulation of Reference 5.

Preparations as prepared in Examples 9–12 hereinafter were subjected to Test examples 11–16 so as to examine the contribution of amino acids or saccharides to the stability of gene in the presence of the absence of collagen.

Example 9

Gene Formulations Containing an Amino Acid (Dried State)

A solution of 10 μg/ml pCAHST-1 and 10 mg/ml arginine, lysine hydrochloride, asparagine, sodium aspartate, glutamine, sodium glutamate, histidine, proline, serine, threonine, glycine, alanine, methionine, valine, or isoleucine, or 5 mg/ml leucine in 150 mM NaCl, 10 mM Tris-HCl (pH7.4) was prepared respectively. One ml portions of each solution was frozen at −40° C., and the frozen products were dried in vacuo overnight at room temperature.

Like this, gene formulations in a dried state were obtained by lyophilization.

Example 10

Gene Formulations Containing a Saccharide (Dried State)

A solution of 10 μg/ml pCAHST-1 and 10 mg/ml trehalose, maltitol, lactose, maltose, glucose, sorbitol, sodium chondroitin sulfate, or xylitol in 150 mM NaCl, 10 mM Tris-HCl (pH7.41 was prepared respectively. Each one ml portion of the solution was frozen at −40° C., and the frozen products were dried in vacuo overnight at room temperature. Like this, gene formulations in a dried state were obtained by lyophilization.

Example 11

Sustained-Release Gene Formulations Containing an Amino Acid (Sponge Form)

A solution of 20 μg/ml of pCAHST-1 (1 ml) and a solution of 40 mg/ml of arginine (125 μl), lysine hydrochloride, asparagine, sodium aspartate, glutamine, sodium glutamate, histidine, proline, serine, threonine, glycine, alanine, methionine, valine, or isoleucine, or 20 mg/ml leucine was respectively combined with a solution of 0.1 w/w % atelocollagen (500mg), so as to prepare the solutions. One ml portion of each solution was frozen at −40° C., and the frozen products were dried in vacuo overnight at room temperature. Like this, gene formulations in a sponge form were obtained by lyophilization.

Example 12

Sustained-Release Gene Formulations Containing a Saccharide (Sponge Form)

A solution of 20 μg/ml of pCAHST-1 (1 ml) and a solution of 40 mg/ml (125 μl) of trehalose, maltitol, lactose, maltose, glucose, sorbitol, sodium chondroitin sulfate, or xylitol was combined respectively with a solution of 0.1 w/w % of atelocollagen (500mg), so as to prepare the solutions. One ml portion of each solution was frozen at −40° C., and the frozen products were dried in vacuo overnight at room temperature. Like this, gene formulations in a sponge form were obtained by lyophilization.

Test Example 11

Figure 14:
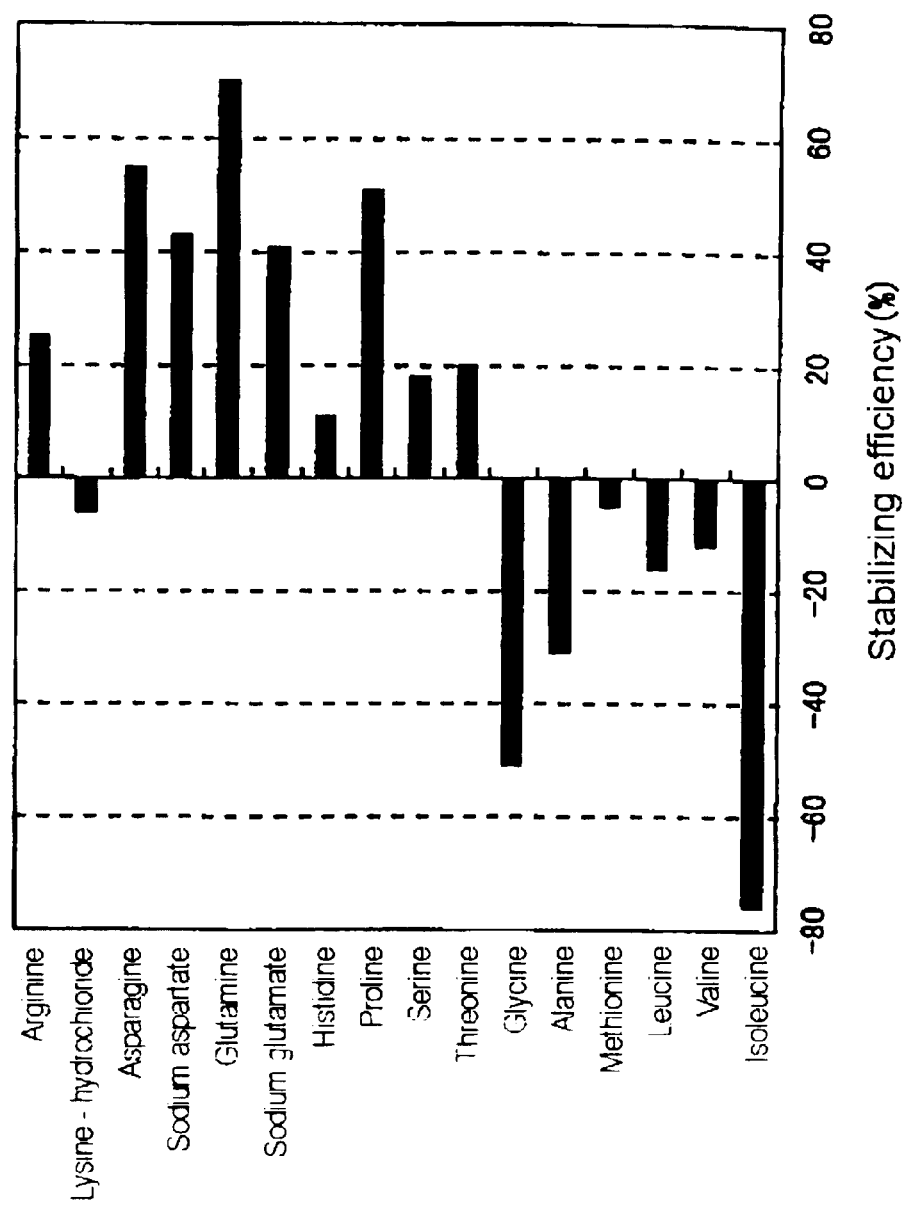
FIG. 14 is a graph which shows the stability of pCAHST-1 at the time of lyophilization, which is comprised in the gene formulations containing the amino acid (Example 9) (Test example 11).

Effect of Amino Acids to Inhibit the Degradation of Gene at the Time of Lyophilization The gene formulations as prepared in Example 9, and the composition as prepared in Reference 1 were dissolved respectively in water immediately after lyophilization, and, in accordance with the procedure described in Test example 1, the solutions were subjected to agarose gel electrophoresis to estimate the primary-structure of pCAHST-1 therein. After the electrophoresis, the gel was stained in ethidium bromide, photographed on a transilluminator, and the picture was scanned in with a photo-scanner. The intensity of the bands containing a supercoiled pDNA (CC), which primary structure was retained, containing a relaxed pDNA (OC) which one site was degraded, and containing a linearized DNA (LS) wherein the pDNA was fragmented to form open-circular one, was computed with an analytic software, and a stabilizing efficiency due to amino acids was calculated according to the following equations. The result is shown in FIG. 14. The order of the amino acids in FIG. 14 reflects the hydrophobicity-hydrophilicity order (Kyte, J. & Doolittele, R. F., 1982, J. Mol. Biol. 157, 105–132). The result demonstrates that the addition of arginine, asparagine, sodium aspartate, glutamine, sodium glutamate, histidine, proline, serine, or threonine to the formulation provided the inhibition of degradation of pCAHST-1, compared to the formulation containing no amino acid.

$$CC \text{ retention ratio of Reference 1 } (\%) = \frac{\text{band intensity of } CC \text{ of Reference 1}}{\text{total band intensity of Reference 1 } (CC + LS + OC)} \times 100$$

$$CC \text{ retention ratio of Example 9 } (\%) = \frac{\text{band intensity of } CC \text{ of Example 9}}{\text{total band intensity of Example 9 } (CC + LS + OC)} \times 100$$

$$\text{Stabilizing efficiency } (\%) = \frac{CC \text{ retention ratio of Example 9 } - CC \text{ retention ratio of Reference 1}}{100 - CC \text{ retention ratio of Reference 1}} \times 100$$

Test Example 12

Figure 15:
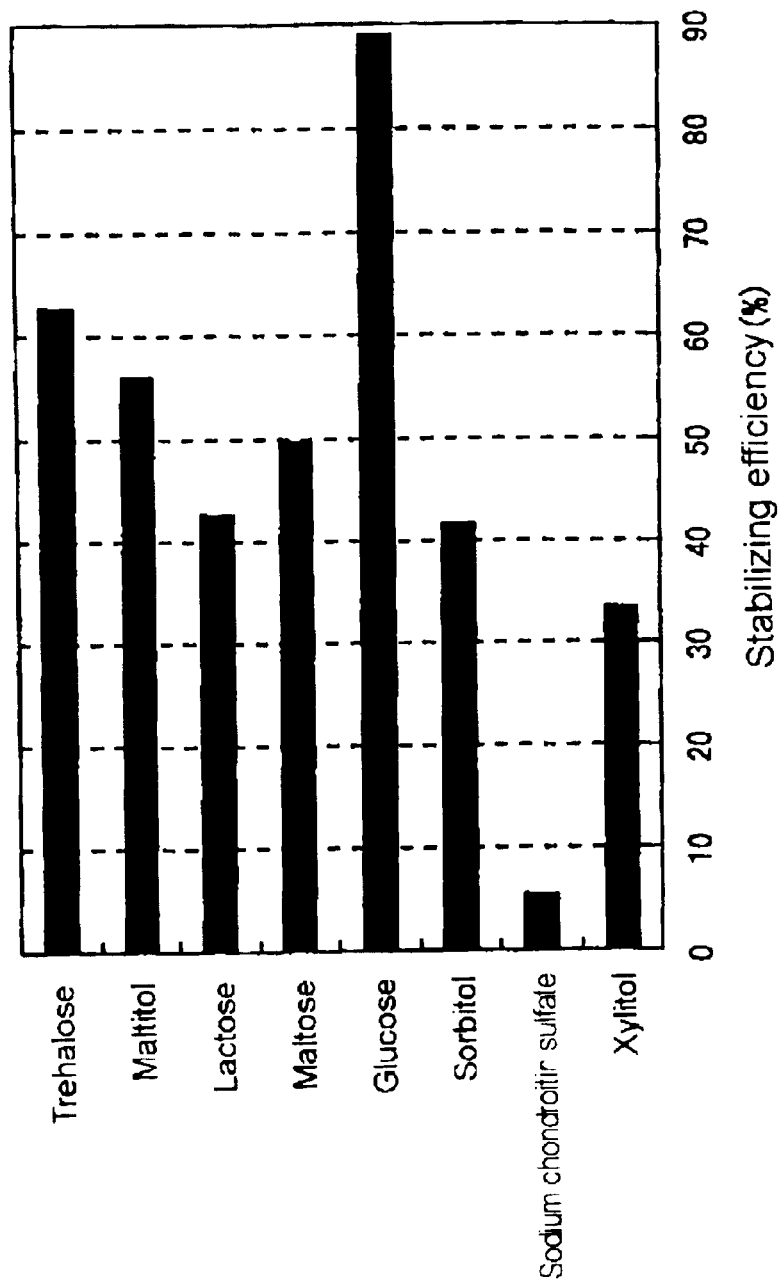
FIG. 15 is a graph which shows the stability of pCAHST-1 at the time of lyophilization, which is comprised in the gene formulations containing the saccharide (Example 10) (Test example 12).

Effect of Saccharides to Inhibit the Degradation of Gene at the Time of Lyophilization The gene formulations as prepared in Example 10, and the composition as prepared in Reference 1 were dissolved respectively in water immediately after lyophilization, and, in accordance with the procedure described in Test example 11, the solutions were subjected to agarose gel electrophoresis to estimate the primary-structure of pCAHST-1 therein. Similarly to the procedure in Test example 11, a stabilizing efficiency was calculated, and the result is shown in FIG. 15. The result demonstrates that the addition of the saccharides to the formulation provided the inhibition of degradation of pCAHST-1, compared to the formulation containing no saccharide.

Test Example 13

Figure 16:
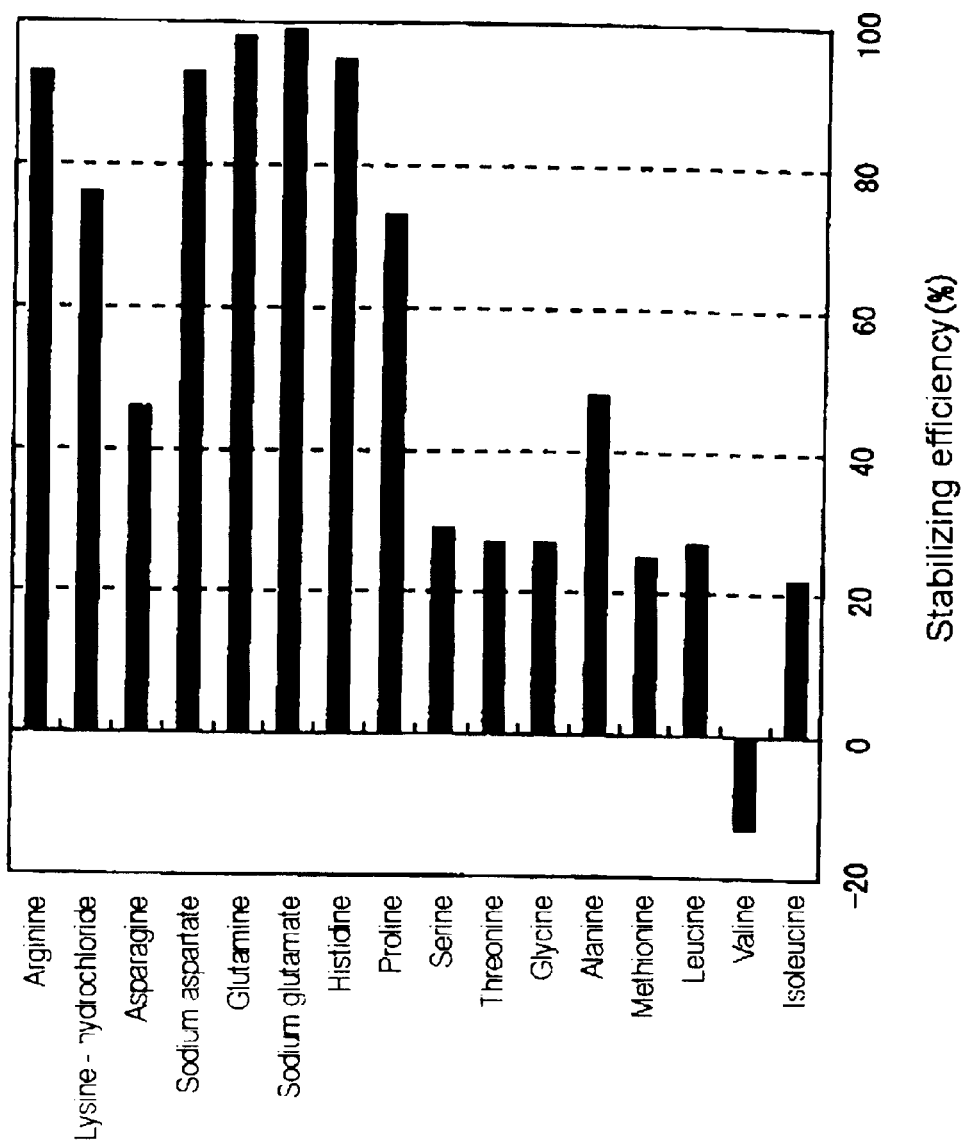
FIG. 16 is a graph which shows the stability of pCAHST-1 at the time of lyophilization, which is comprised in the gene formulations containing atelocollagen, and the amino acid (Example 11) (Test example 13).

Effect of Amino Acids to Inhibit the Degradation of Gene in the Presence of Collagen The gene formulations in a sponge form as prepared in Example 11, and the composition in a sponge form as prepared in Reference 4 were dissolved respectively in a solution of 150 mM NaCl, 10 mM Tris-HCl (pH7.4) under heating, and the solutions were treated with a collagenase. After the treatment, the solutions were subjected to agarose gel electrophoresis to estimate the primary-structure of pCAHST-1 therein, in accordance with the procedure described in Test example 11. Similarly to the procedure in Test example 11, a stabilizing efficiency was calculated, and the result is shown in FIG. 16. The order of the amino acids in FIG. 16 reflects the hydrophobicity-hydrophilicity order (Kyte, J. & Doolittele, R. F., 1982, J. Mol. Biol. 157, 105–132). The result demonstrates that the addition of the amino acids to the formulation provided the drastic inhibition of degradation of pCAHST-1, compared to the formulation containing no amino acid.

Test Example 14

Figure 17:
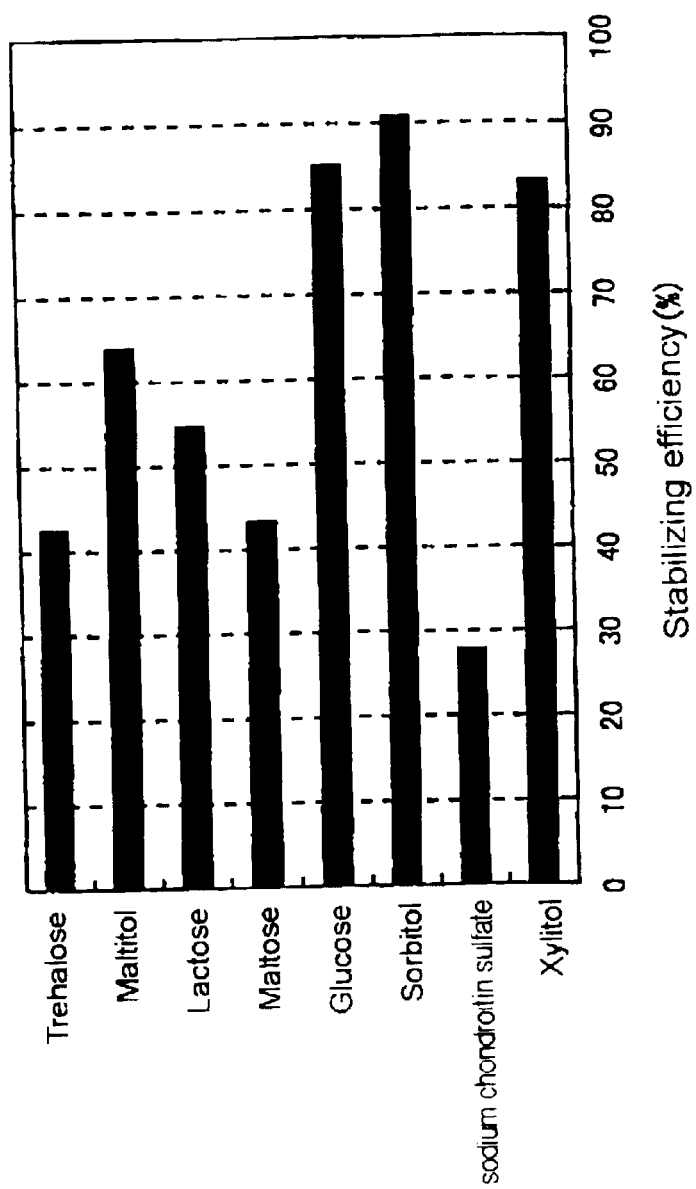
FIG. 17 is a graph which shows the stability of pCAHST-1 at the time of lyophilization, which is comprised in the gene formulations containing atelocollagen, and the saccharides (Example 12) (Test example 14).

Effect of Saccharides to Inhibit the Degradation of Gene in the Presence of Collagen The gene formulations in a sponge form as prepared in Example 12, and the composition in a sponge form as prepared in Reference 4 were dissolved respectively in a solution of 150 mM NaCl, 10 mM Tris-HCl (pH7.4) under heating, and the solutions were treated with a collagenase. After the treatment, the solutions were subjected to agarose gel electrophoresis to estimate the primary-structure of pCAHST-1 therein, in accordance with the procedure described in Test example 11. Similarly to the procedure in Test example 11, a stabilizing efficiency was calculated, and the result is shown in FIG. 17. Addition of saccharides to the formulation enabled the drastic inhibition of degradation of pCAHST-1, compared to the formulation containing no saccharide.

Test Example 15

Effect of Amino Acids and Saccharides to Inhibit the Degradation of Gene at the Time of Preservation at 40° C.

Figure 18:
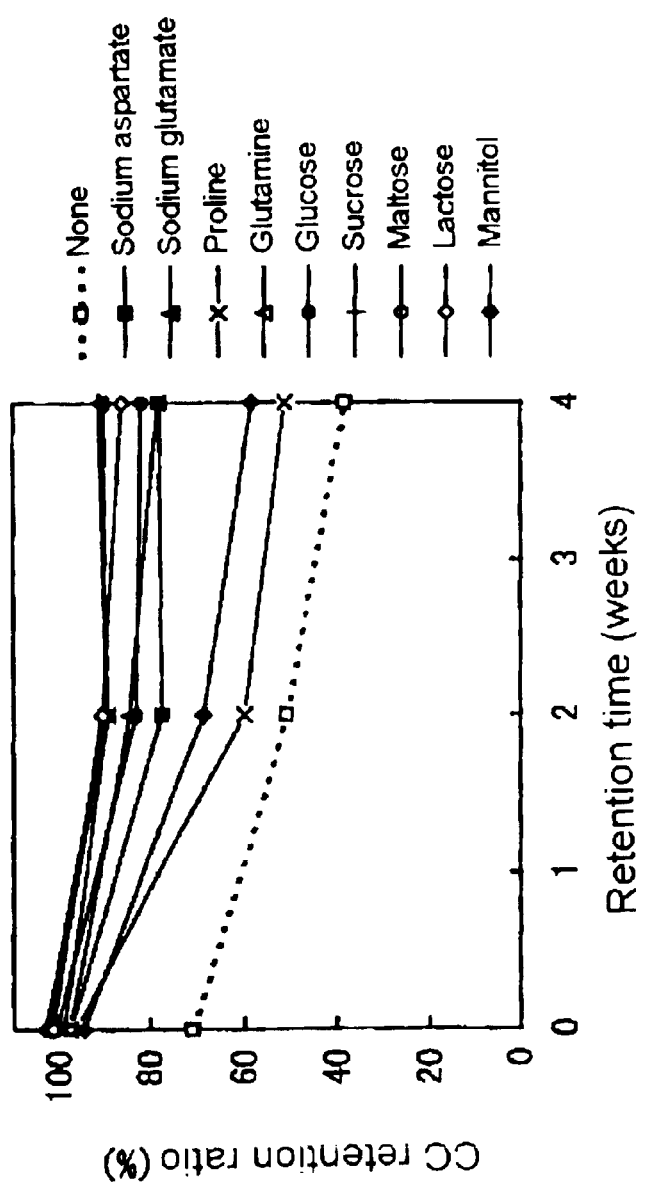
FIG. 18 is a graph which shows the stability of pCAHST-1 comprised in the gene formulations containing the amino acid (Example 10), which formulations have been preserved at 40 ° C. (Test example 15).

The gene formulations in a dried state containing sodium aspartate, monosodium glutamate, proline, or glutamine of the formulations as prepared in Example 9; the gene formulations in a dried state containing glucose, sucrose, maltose, lactose, or mannitol; and the compositions as prepared in Reference 1 were preserved for one, two, and four weeks at 40° C. In accordance with the procedure described in Test example 1, the primary-structure of pCAHST-1 therein was estimated by agarose gel electrophoresis after the preservations. The result is shown in FIG. 18. The result demonstrates that the addition of the non-hydrophobic amino acids or the saccharides to the formulation drastically improved the preservative stability of pCAHST-1 under the specified conditions, compared to the formulation containing none of them.

Test Example 16

Effect of Amino Acids and Saccharides to Inhibit the Degradation of Gene at the Preservation of Gene Formulations Containing Collagen at 40° C.

Figure 19:
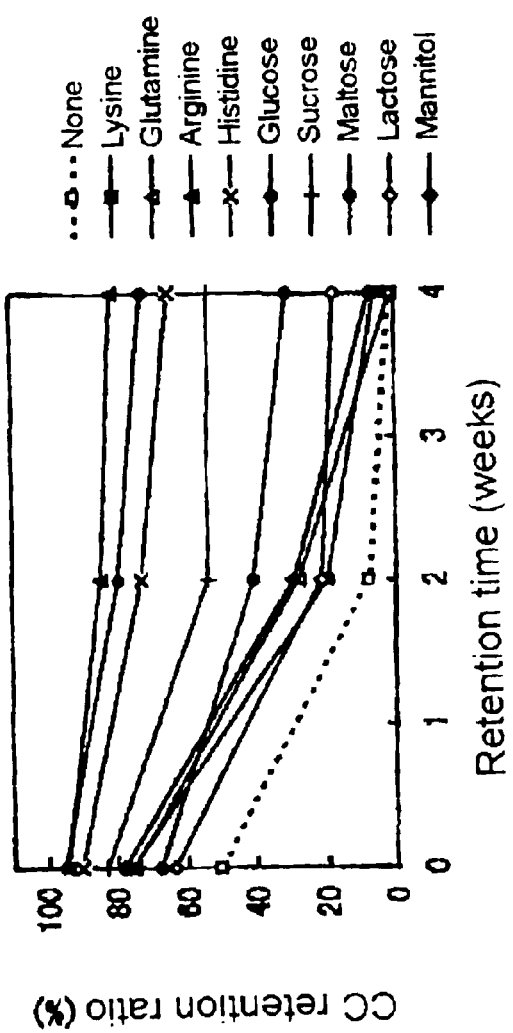
FIG. 19 is a graph which shows the stability of pCAHST-1 comprised in the gene formulations containing atelocollagen, and the amino acid (Example 11), which formulations have been preserved at 40° C. (Test example 16).

The gene formulations in a dried state containing lysine, glutamine, arginine, or histidine of the formulations as prepared in Example 11; the gene formulations in a dried state containing glucose, sucrose, maltose, lactose, or mannitol; and the compositions as prepared in Reference 4 were preserved for one, two, and four weeks at 40° C. In accordance with the procedure described in Test example 13, the primary-structure of pCAHST-1 therein was estimated by agarose gel electrophoresis after the preservations. The result is shown in FIG. 19. The result demonstrates that the addition of the amino acid or the saccharide to the formulation drastically improved the preservative stability of pCAHST-1 under the specified conditions, compared to the formulation containing none of them.

EFFECTS OF THE INVENTION

The result of effects of the present formulations to inhibit the degradation of gene obtained in test example 1 to 9 are summarized as shown in Table 9.

TABLE 9

The effects of the present formulations to inhibit the degradation of gene
(1) Stability at the time of lyophilization

| i) without any additive | | a) | b) |
|---|---|---|---|
| control | | 72% | (76%) |
| amino acid: | glycine | 79% | |
| | alanine | 83% | |
| | lysine | 84% | |
| | aspartic acid | | (91%) |
| | glutamic acid | 96% | (103%) |
| | | c) | |
| control | | 78% | |
| saccharide: | glucose | 95% | |
| | sucrose | 96% | |
| | maltose | 95% | |
| | lactose | 100% | |
| | mannitol | 95% | |
| | | b) | |
| control | | 76% | |
| organic acid: | tartaric acid | 95% | |
| | citric acid | 102% | |
| ii) with an additive | | | |
| (collagen) | | d) | |
| control | | 85% | |
| stabilizing agent: | glucose | 94% | |
| | sucrose | 95% | |
| | glutamic acid | 95% | |
| (DMRIE-C) | | e) | |
| control | | 69% | |
| stabilizing agent: | sucrose | 100% | |

Note: a) Test example 1 (Table 1), b) Test example 3 (Table 3),
c) Test example 2 (Table 2), d) Test example 8 (Table 7), TABLE 9-continued

| | | | | |
|---|---|---|---|---|
| e) Test example 4 (Table 4) | | | | |
| (2) Preservative stability of lyophilized formulations | | | | |
| i) without any additive | | c) | f) | f) f) |
| (40° C.) | | (lyophilized) | after 1 week | after 2 weeks after 4 weeks |
| control | | (78%) | 67% | 56% 34% |
| stabilizing agent: | glucose | (95%) | 92% | 91% 71% |
| ii) with an additive | (DMRIE-C) | | | |
| (37° C.) | | e) | g) | |
| | | (lyophilized) | after 4 weeks | |
| control | | (69%) | 8.5% | |
| stabilizing agent: | sucrose | (100%) | 67% | |
| Note: f) Test example 5 (Table 5), g) Test example 6 (Table 6) | | | | |
| (3) Stability at the time of gelling/kneading | | | | |
| (at making bar formulations by kneading of lyophilized materials) | | | | |
| | | d) | h) | |
| | | (lyophilized) | after making rod formulation | |
| control | | (85%) | 66% | |
| stabilizing agent: | glucose | | | |
| additive: | collagen | (95%) | 92% | |
| Note: h) Test example 8 (Table 8) | | | | |
| (4) Preservative stability of the formulation in form of aqueous solution | | | | |
| | | | 1) | |
| (40° C.) | | | after 4 weeks | |
| control | | | vector not detected | |
| stabilizing agent: | glucose | | | |
| additive: | DMRIE-C | | vector remains | |
| Note: l) Test example 7 (FIG. 7) | | | | |

INDUSTRIAL APPLICABILITY

Gene formulation which comprises a gene or a vector incorporated with a gene wherein the gene or the vector demonstrates an improved stability are utilized safely and readily in gene therapy, which therapy would be applied frequently from now on. The formulation of the present invention provides a basis for the gene therapy to be prevalent. Especially, the present formulation makes it possible to distribute or preserve the gene or the vector incorporated with the gene at an ambient temperature, and, therefore, provide DNA vaccines capable to be used in a location where cold chines have not been accomplished.

What is claimed is:

1. A method for stabilizing a closed circular DNA molecule in a formulation, comprising:
    adding citric acid or tartaric acid, or a salt thereof, to an aqueous solution of the closed circular DNA and atelocollagen, and
    lyophilizing the solution.

2. The method of claim 1, wherein the aqueous solution of the closed circular DNA further comprises a cationic lipid, a cationic polymer or a hydrophobic polymer.

3. The method of claim 2, wherein the amount of citric acid or tartaric acid is not less than 1% w/v of the aqueous solution of the closed circular DNA.

4. The method of claim 1, wherein the amount of citric acid or tartaric acid is not less than 1% w/v of the aqueous solution of the closed circular DNA.

5. A method for stabilizing a closed circular DNA molecule in a formulation, comprising:
    adding atelocollagen to an aqueous solution of the closed circular DNA and citric acid or tartaric acid or both citric acid and tartaric acid, or a salt thereof, and
    lyophilizing the solution.

6. The method of claim 5, wherein the aqueous solution of the closed circular DNA further comprises a cationic lipid, a cationic polymer or a hydrophobic polymer.

7. The method of claim 6, wherein the amount of citric acid or tartaric acid is not less than 1% w/v of the aqueous solution of the closed circular DNA.

8. The method of claim 5, wherein the amount of citric acid or tartaric acid is not less than 1% w/v of the aqueous solution of the closed circular DNA.

* * * * *